United States Patent
Hulvershorn et al.

(10) Patent No.: US 8,262,714 B2
(45) Date of Patent: Sep. 11, 2012

(54) TECHNIQUES FOR SELECTING SIGNAL DELIVERY SITES AND OTHER PARAMETERS FOR TREATING DEPRESSION AND OTHER NEUROLOGICAL DISORDERS, AND ASSOCIATED SYSTEMS AND METHODS

(75) Inventors: Justin Hulvershorn, Seattle, WA (US); Bradford E. Gliner, Sammamish, WA (US); Brian Kopell, Milwaukee, WI (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 815 days.

(21) Appl. No.: 12/395,257

(22) Filed: Feb. 27, 2009

(65) Prior Publication Data
US 2010/0036453 A1   Feb. 11, 2010

Related U.S. Application Data

(60) Provisional application No. 61/086,199, filed on Aug. 5, 2008.

(51) Int. Cl.
*A61N 5/055* (2006.01)
*A61N 1/36* (2006.01)

(52) U.S. Cl. .................. 607/88; 607/3; 607/45
(58) Field of Classification Search ............ 607/88, 607/3, 45; 600/411
See application file for complete search history.

(56) References Cited

U.S. PATENT DOCUMENTS

| | | |
|---|---|---|
| 4,883,057 A | 11/1989 | Broderick |
| 5,540,734 A | 7/1996 | Zabara |
| 5,611,350 A | 3/1997 | John |
| 5,792,186 A | 8/1998 | Rise |
| 5,921,245 A | 7/1999 | O'Donnell, Jr. |

(Continued)

FOREIGN PATENT DOCUMENTS
WO    WO 0197906    12/2001
(Continued)

OTHER PUBLICATIONS

Al-Hakim, R. et al., "A Dorsolateral Prefrontal Cortex Semi-Automatic Segmenter," Proceedings of the SPIE Medical Imaging 2006; 6144: 170-177.

(Continued)

*Primary Examiner* — Carl H. Layno
*Assistant Examiner* — Jon-Eric C. Morales
(74) *Attorney, Agent, or Firm* — Christopher S. L. Crawford; Craig Hoersten; Peter R. Lando

(57) ABSTRACT

The present disclosure is directed generally to techniques for selecting signal delivery sites and other signal delivery parameters for treating depression and other neurological disorders, and associated systems and methods. A method in accordance with a particular embodiment includes obtaining first imaging information corresponding to a first region of a patient's brain, the first imaging information being based at least in part on functional characteristics of the first region. The method further includes obtaining second imaging information corresponding to a second region of the patient's brain, the second region being a subset of the first region, the second imaging information being based at least in part on functional or structural characteristics of the second region. A target neural population is then selected based at least in part on the second imaging information. The method still further includes applying an electromagnetic signal to the target neural population to improve a patient function.

14 Claims, 7 Drawing Sheets

U.S. PATENT DOCUMENTS

| | | | |
|---|---|---|---|
| 5,938,688 | A | 8/1999 | Schiff |
| 5,975,085 | A | 11/1999 | Rise |
| 6,016,449 | A | 1/2000 | Fischell et al. |
| 6,128,537 | A | 10/2000 | Rise |
| 6,132,361 | A | 10/2000 | Epstein et al. |
| 6,161,045 | A | 12/2000 | Fischell et al. |
| 6,176,242 | B1 | 1/2001 | Rise |
| 6,216,030 | B1 | 4/2001 | Howard et al. |
| 6,230,049 | B1 | 5/2001 | Fischell et al. |
| 6,263,237 | B1 | 7/2001 | Rise |
| 6,353,754 | B1 | 3/2002 | Fischell et al. |
| 6,366,813 | B1 | 4/2002 | DiLorenzo |
| 6,418,344 | B1 | 7/2002 | Rezai |
| 6,425,852 | B1 | 7/2002 | Epstein et al. |
| 6,463,328 | B1 | 10/2002 | John |
| 6,473,639 | B1 | 10/2002 | Fischell et al. |
| 6,591,138 | B1 | 7/2003 | Fischell |
| 6,597,954 | B1 | 7/2003 | Pless et al. |
| 6,609,030 | B1 | 8/2003 | Rezai et al. |
| 6,609,031 | B1 | 8/2003 | Law et al. |
| 6,708,064 | B2 | 3/2004 | Rezai |
| 6,735,475 | B1 | 5/2004 | Whitehurst et al. |
| 6,782,292 | B2 | 8/2004 | Whitehurst |
| 6,819,956 | B2 | 11/2004 | DiLorenzo |
| 6,871,098 | B2 | 3/2005 | Nuttin et al. |
| 6,907,280 | B2 | 6/2005 | Bacerra et al. |
| 7,010,351 | B2 | 3/2006 | Firlik et al. |
| 7,346,395 | B2 | 3/2008 | Lozano et al. |
| 7,353,065 | B2 | 4/2008 | Morrell |
| 7,653,433 | B2 | 1/2010 | Lozano et al. |
| 7,684,866 | B2 | 3/2010 | Fowler et al. |
| 2002/0013612 | A1 | 1/2002 | Whitehurst |
| 2002/0058867 | A1 | 5/2002 | Breiter et al. |
| 2002/0062143 | A1 | 5/2002 | Baudino et al. |
| 2002/0087201 | A1 | 7/2002 | Firlik et al. |
| 2002/0091419 | A1 | 7/2002 | Firlik |
| 2002/0151939 | A1 | 10/2002 | Rezai |
| 2002/0169485 | A1 | 11/2002 | Pless et al. |
| 2003/0028072 | A1 | 2/2003 | Fischell et al. |
| 2003/0097159 | A1 | 5/2003 | Schiff et al. |
| 2003/0149457 | A1 | 8/2003 | Tcheng et al. |
| 2003/0181954 | A1 | 9/2003 | Rezai |
| 2004/0172091 | A1 | 9/2004 | Rezai |
| 2004/0186532 | A1 | 9/2004 | Tadlock |
| 2005/0021118 | A1 | 1/2005 | Genau et al. |
| 2005/0027284 | A1 | 2/2005 | Lozano et al. |
| 2005/0033378 | A1 | 2/2005 | Sheffield et al. |
| 2005/0033379 | A1 | 2/2005 | Lozano et al. |
| 2005/0143799 | A1 | 6/2005 | Black et al. |
| 2005/0143800 | A1 | 6/2005 | Lando et al. |
| 2006/0004422 | A1 | 1/2006 | De Ridder |
| 2006/0015153 | A1 | 1/2006 | Gliner et al. |
| 2006/0106430 | A1 | 5/2006 | Fowler et al. |
| 2006/0212090 | A1 | 9/2006 | Lozano et al. |
| 2006/0212091 | A1 | 9/2006 | Lozano et al. |
| 2006/0259094 | A1 | 11/2006 | Naisberg et al. |
| 2007/0203545 | A1 | 8/2007 | Stone |
| 2007/0244519 | A1 | 10/2007 | Keacher et al. |
| 2007/0265489 | A1 | 11/2007 | Fowler et al. |
| 2007/0288072 | A1* | 12/2007 | Pascual-Leone et al. ........ 607/88 |
| 2008/0064947 | A1 | 3/2008 | Heruth et al. |
| 2008/0103548 | A1 | 5/2008 | Fowler et al. |
| 2008/0208285 | A1 | 8/2008 | Fowler et al. |
| 2009/0112281 | A1 | 4/2009 | Miyazawa et al. |
| 2009/0131995 | A1 | 5/2009 | Sloan |
| 2009/0149898 | A1 | 6/2009 | Hulvershorn et al. |
| 2010/0036453 | A1 | 2/2010 | Hulvershorn et al. |
| 2010/0057159 | A1 | 3/2010 | Lozano |

FOREIGN PATENT DOCUMENTS

| | | |
|---|---|---|
| WO | WO 03043690 | 5/2003 |

OTHER PUBLICATIONS

Baer, D.M. et al., "Some Current Dimensions of Applied Behavior Analysis," Journal of Applied Behavior Analysis, No. 1, Spring 1968, pp. 91-97.

Barbas et al. "Topographically Specific Hippocampal Projections Target Functionally Distinct Prefrontal Areas in the Rhesus Monkey," Hippocampus vol. 5, 1995, pp. 511-533.

Barbas et al., "Projections from the Amygdala to Basoventral and Mediodorsal Prefrontal Regions in the Rhesus Monkey," The Journal of Comparative Neurology, vol. 300, 1990, pp. 549-571.

Barr, Deborah et al., "Induction and Reversal of Long-Term Potentiation by Low- and High-Intensity Theta Pattern Stimulation," The Journal of Neuroscience, 15(7): pp. 5402-5410 (Jul. 1995).

Barres et al., "Proliferation of oligodendrocyte precursor cells depends on electrical activity in axons," Nature; Medical Research Council Developmental Neurobiology Programme, Department of Biology, University College, London, p. 258-260, (Jan. 21, 1993).

Behrens, T. et al., "Non-invasive mapping of connections between human thalamus and cortex using diffusion imaging," Nature neuroscience, vol. 6 No. 7, pp. 750-757 (Jul. 2003).

Bel, S. and Bauer, B.L., "Dorsal Column Stimulation (DCS): Cost to Benefit Analysis," Acta Neurochirurgica, Suppl. 52, pp. 121-123 (1991).

Benabid, A.L. et al., "Chronic electrical stimulation of the ventralis intermedius nucleus of the thalamus as a treatment of movement disorders," J. Neurosurg., Apr. 1997, 86(4); 737; http:--www.ncbi.nlm.nih.gov; [accessed Nov. 18, 2003].

Berument, S.K. et al., "Autism Screening Questionaire: Diagnostic Validity," British Journal of Psychiatry, vol. 175, 1999, pp. 444-451.

Beveridge, J. A., "Use of Exogenous Electric Current in the Treatment of Delayed Lesions in Peripheral Nerves," Plastic and Reconstructive Surgery, Oct. 1988, vol. 82, No. 4, pp. 573-579.

Bezard et al., "Cortical Stimulation and Epileptic Seizure: A Study of the Potential Risk in Primates," Neurosurgery, vol. 45, No. 2, Aug. 1999, 346-350.

Binder, J. M.D., "Functional Magnetic Resonance Imaging: Language Mapping," Neurosurgery Clinics of North America, vol. 8, No. 3, Jul. 1997, pp. 383-392.

Bjorklund et al., "Cell replacement therapies for central nervous system disorders," Commentary, Nature Neuroscience, vol. 3, No. 6, Jun. 2000, pp. 537-544.

Bluestone, Avraham Y. et al., "Three-dimensional optical tomography of hemodynamics in the human head," Optics Express, vol. 9, No. 6, pp. 272-286 (Sep. 10, 2001).

Boisgueheneuc, F. et al., "Functions of the Left Superior Frontal Gyrus in Humans: A Lesion Study," Brain, Oxford University Press. Advance Access publication Sep. 1, 2006, pp. 3315-3328.

Bozkurt, Alper et al., "A Portable Near Infrared Spectroscopy System for Bedside Monitoring of Newborn Brain," BioMedical Engineering OnLine 2005, 4:29, pp. 1-11.

Brain Electrical Stimulation to Enhance Recovery After Stroke, ClinicalTrials.gov, URL: http://www.clinicaltrials.gov/ct/show/NCT00085657?order=2 [Retrieved on Dec. 22, 2005].

Bremner, et al., "Reduced volume of orbitofrontal cortex in major depression," Biological Psychiatry, Feb. 2002, 51:4, 273-279.

Bremner, J.D., "Structural Changes in the Brain in Depression and Relationship to Symptom Recurrence," CNS Spectrums, vol. 7, No. 2 Feb. 2002, pp. 129-139.

Browne et al., "Concurrent cervical and craniofacial pain," Review Article, Oral Surgery, Oral Medicine, Oral Pathology, vol. 86, No. 6, Dec. 1998, pp. 633-640.

Budson et al., "Memory Dysfunction," N. Eng. J. Med., 352(7): 692-699, 2005.

Burnett, Mark G. et al., "Diffuse optical measurement of blood flow, blood oxygenation, and metabolism in a human brain during sensorimotor cortex activation," Optics Letters, vol. 29, No. 15, pp. 1766-1768 (Aug. 1, 2004).

Bury, Scott et al., "The Effects of Behavioral Demand on Motor Cortical and Cerebellar Structural Plasticity After Brain Injury in Adult Rats," http://www.mcmaster.ca-inabis98-schallert-bury0827-two.html#introduction, 2 pages [Retrieved on Mar. 1, 2003].

Butefisch et al., "Mechanisms of use-dependent plasticity in the human motor cortex," Proc. Natl. Acad. Sci. USA, vol. 97, No. 7, pp. 3661-3665 (Mar. 2000).

Caetano et al., "Anatomical MRI Study of Hippocampus and Amygdalia in Patients with Current and Remitted Major Depression," Psychiatry Research: Neuroimaging vol. 132, 2004, pp. 141-147.

Canavero, S. and Paolotti, R., "Extradural Motor Cortex Stimulation for Advanced Parkinson's Disease: Case Report," Movement Disorders, Jan. 2000, 15(1):169-171.

Cao, Yue et al., "Cortical Language Activation in Stroke Patients Recovering From Aphasia With Functional MRI," Stroke, vol. 30, pp. 2331-2340, Nov. 1999.

Capel et al, "The influence of electrostimulation on hexobarbital induced loss of righting reflex in rats," Acupunct Electrother. Res. 7(1): 17-26, 1982.

Carroll et al., "Motor cortex stimulation for chronic neuropathic pain: a preliminary study of 10 cases," Pain, 84, Feb. 2000, pp. 431-437. Elsevier Science, B.V.

Castro, Raymond et al., "Failure of Bone Marrow Cells to Transdifferentiate into Nueral Cells in Vivo," Science 297: 1299, Aug. 2002.

Chance, Britton et al., "A Novel Method for Fast Imaging of Brain Function, Non-Invasively, with Light," Optics Express, vol. 2, No. 10, May 1998, pp. 411-423.

Chapter 18/ The Functional Organization of Prception and Movement, p. 347.

Cheun et al., "Differentiation of a Stem Cell Line Toward a Neuronal Phenotype," Int. J. Devl. Neuroscience, vol. 9, No. 4, pp. 391-404 (1991).

Cicinelli et al., "Transcranial magnetic stimulation reveals an interhemispheric asymmetry of cortical inhibition in focal epilepsy," Neurophysiology, vol. 11, No. 4 Mar. 20, 2000, pp. 701-707.

Cincotta et al., "Reorganization of the motor cortex in a patient with congenital hemiparesis and mirror movements," Neurology, Jul. 12, 2000, 5+A535(1), pp. 129-131.

Cincotta et al., "Suprathreshold 0.3 Hz repetitive TMS prolongs the cortical silent period: potential implications for therapeutic trials in epilepsy," Clinical Neurophysiology, vol. 114, 2003, pp. 1827-1833, Elsevier Ireland Ltd.

Classen et al., "Rapid Plasticity of Human Cortical Movement Representation Induced by Practice," The Journal of Neurophysiology, vol. 79, No. 2, pp. 1117-1123 (Feb. 1998).

CNN.com, Health, "Lab Zaps Strokes with Magnetic Pulses," http://www.cnn.com/2004/HEALTH/conditions/11/29/zapping.strokes.ap/, Nov. 29, 2004, 4 pages. [Retrieved on Dec. 2, 2004].

Cohen et al., "Studies of Neuroplasticity With Transcranial Magnetic Stimulation," The Journal of Clinical Neurophysiology, vol. 15, No. 4 (1998).

Color Picture of the Brain (1 pg) date unknown.

Cosgrove et al. "Psychosurgery," Neurosurgery Clinicals of North America vol. 6 No. Jan. 1995. pp. 167-176.

Cramer et al., "Use of Functional MRI to Guide Decisions in a clinical Stroke Trial," Stroke, Journal of the American Heart Association, May 2005, pp. e50-e52, American Heart Association, Dallas TX.

Cramer, S.C. and Bastings, E.P., "Mapping clinically relevant plasticity after stroke," Neuropharmacology vol. 19, No. 5, pp. 842-851 (Apr. 2000).

Cutrer et al., "Effects of PNU-109,291, a selective 5-HT$_{1D}$ receptor agonist, on electrically induced dural plasma extravasation and capsaicin-evoked c-fos immunoreactivity within trigeminal Nucleus caudalis," Neuropharmacology, 38, 1999, pp. 1043-1053, Pergamon Press, U.K.

Cytokines Web Clinical Significance, Cytokines Web, 2 pages, URL: http:-- cmbi.bjmu.edu.cn-cmbidata-cgf-CGF__Database-cytweb-roles-index.html [Retrieved on Sep. 2, 2005].

Daley, George et al., "Realistic Prospects for Stem Cell Therapeutics," Hematology 398-418 (2003).

Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).

Dawes, Sharen E., "The Mesulam & Weintraub Cancellation Test: Australian Normative Data and Clinical Utility", University of Southern Queensland, Oct. 27, 2000. [Retrieved on Sep. 12, 2005]. Retrieved from the internet <URL http://www.usq.edu.au/users/senior/Theses/Dawes%20Thesis/Dawes%20Introduction.htm>.

Dawson, G. et al., "Neural Correlates of Face and Object Recognition in Young Children with Autism Spectrum Disorder, Developmental Delay, and Typical Development," Child Development, vol. 73, No. 3, 2002, pp. 700-717.

De Ridder, Dirk et al., "Magnetic and electrical stimulation of the auditory cortex for intractable tinnitus," Journal Neurosurg., vol. 100, pp. 560-564, (Mar. 2004).

Delbello et al., "Magnetic Resonance Imaging Analysis of Amygdala and other Subcortical Brain Regions in Adolescents with Bipolar Disorders," Bipolar Disorders vol. 6, 2004, pp. 43-52.

Devinsky et al., "Clinical and electroencephalographic features of simple partial seizures," Neurology, 38, Sep. 1988, pp. 1347-1352.

Devinsky et al., "Electroencephalographic studies of simple partial seizures with subdural electrode recordings," Neurology, 39, Apr. 1989, pp. 527-533.

Di Lazzaro, V. et al., "Theta-burst repetitive transcranial magnetic stimulation suppresses specific excitatory circuits in the human motor cortex," Physiology in Press; published online on Apr. 21, 2005 as 10.1113-jphysiol.2005.087288.

Diamond et al., "Preclinical Research on Stress, Memory and the Brain in the Development of Pharmacotherapy for Depression," European Neuropsychopharmacology vol. 14, 2004 pp. S491-S495.

Ding, Yuemin et al., "Neural Plasticity After Spinal Cord Injury," Current Pharmaceutical Design vol. 11, No. 11, pp. 1441-1450, Abstract Only, 1 page (Apr. 2005).

Dougherty et al., "Cerebral metabolic correlates as potential predictors of response to anterior cingulotomy for treatment of major depression," J. Neurosurg., 99(6): 1010-7, 2003.

Drevets et al. "Functional Anatomical Correlates of Antidepressants Drug Treatment Assessed Using PET Measures of Regional Glucose Metabolism," European Neuropsychopharmology vol. 12, 2002, pp. 527-544.

Drevets et al. "Subgenal Prefrontal Cortex Abnormalities in Mood Disorders," Nature vol. 386, Apr. 24, 1997, pp. 824-827.

Duncan, Pamela W. et al., "Defining post-stroke recovery: implications for design and interpretation of drug trials," Neuropharmacology vol. 39, pp. 835-841 (2000).

Ebmeier et al. "Cerebral Perfusion Correlates of Depressed Mood," British Journal of Psychiatry vol. 178, 1997, pp. 77-81.

Feindel et al., "The tentorial nerves and localization of intracranial pain in man," Neurology, 10, 1960, 555-563.

Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam, NL.

Feys et al., "Value of somatosensory and motor evoked potentials in predicting arm recovery after a stroke," (Oct. 1999).

Fossati et al., "Neuroplasticity: from MRI to Depressive Symptoms," European Neuropsychophamacology vol. 14, 2004, pp. S503-S510.

Foster et al., "Transmitter expression and morphological development of embryonic medullary and mesencephalic raphé neurones after transplantation to the adult rat central nervous system. III. Grafts to the striatum," Exp Brain Res, Apr. 1988, 70(2):225-41, Springer Berlin/Heidelber.

Fraichard et al., "In vitro differentiation of embryonic stem cells into glial cells and functional neurons," Journal of Cell Science, 1995, vol. 108, issue 10, pp. 3181-3188, Great Britain.

Franzini et al., "Reversal of thalamic hand syndrome by long-term motor cortex stimulation," Journal of Neurosurgery 93(5):873-875, Nov. 2000.

Fregni et al., "Antiepileptic Effects of Repetitive Transcranial Magnetic Stimulation in Patients with Cortical Malformations: An EEG and Clinical Study," ASSFN Proceedings 2004, Stereotactic and Functional Neurosurgery, 2005, 83:57-62.

Fregni, Felipe et al., "Anodal Transcranial Direct Current Stimulation of Prefrontal Cortex Enhances Working Memory," Experimental Brain Research vol. 166, No. 1, pp. 23-30 (Sep. 2005).

Galynker et al. "Hypofrontality and Negative Symptoms in Major Depressive Disorder," The Journal of Nuclear Medicine vol. 39, No. 4, Apr. 1998, pp. 608-612.

Gash, D. M. et al., "Amitotic Neuroblastoma Cells Used for Neural Implants in Monkeys," Science, Sep. 26, 1986, vol. 233, No. 4771, pp. 1420-1422, Copyright © 1986 by American Association for the Advancement of Science.

Genesis Patient Programmer; 1 pg; http://www.ans-medical.com/physicians/GenesisIPGSystem/SystemOverview.html; [accessed Apr. 16, 2003].

Gladstone et al., "Enhancing Recovery after Stroke with Noradrenergic Pharmacotherapy: A New Frontier?" Can J. Neurol. Sci., vol. 27, No. 2, May 2000, pp. 97-105.

Goadsby et al., "Differential effects of low dose CP122,288 and eletriptan on Fos expression due to stimulation of the superior sagittal sinus in cat," Pain, 82, 1999, pp. 15-22, Elsevier Science, B.V.

Goadsby et al., "Stimulation of an intracranial trigeminally-innervated structure selectively increases cerebral blood flow," Brain Research, 751(2), 1997, pp. 247-252, Elsevier Science, B.V.

Goadsby et al., "Substance P Blockade with the Potent and Centrally Acting Antagonist GR205171 Does Not Effect Central Trigeminal Activity with Superior Sagittal Sinus Stimulation," Neuroscience, 1998, vol. 86, No. 1, pp. 337-343, Pergamon Press, U.K.

Goadsby et al., "The Trigeminovascular System and Migraine: Studies Characterizing Cerebrovascular and Neuropeptide Changes Seen in Humans and Cats," Annals of Neurology, Jan. 1993, vol. 33, No. 1, pp. 48-56.

Goldapple et al., "Modulation of Cortical-Limbic Pathways in Major Depression," Arch Gen Psychiatry, vol. 61, Jan. 2004, pp. 34-41.

Gordon et al., "Parameters for direct cortical electrical stimulation in the human: histopathologic confirmation," Electroencephalography and clinical Neurophysiology, vol. 75, pp. 371-377 (1990).

Gupta et al., "Differentiation Characteristics of Human Neuroblastoma Cells in the Presence of Growth Modulators and Antimitotic Drugs," Developmental Brain Research, 19(1985)21-29, Elsevier.

Haberler et al., "No Tissue Damage by Chronic Deep Brain Stimulation in Parkinson's Disease," Annals of Neurology, vol. 48, No. 3, Sep. 2000, pp. 372-376.

Hagemann, Georg et al., "Increased Long-Term Potentiation in the Surround of Experimentally Induced Focal Cortical Infarction," Annals of Neurology, vol. 44, No. 2, pp. 255-258 (Aug. 1998).

Haglund, Michael M. et al., "Optical imaging of epileptiform and functional activity in human cerebral cortex," Nature, Aug. 20, 1992, pp. 668-671, vol. 358, Nature Publishing Group.

Haldane et al., "New Insights Help Define the Pathophysiology of Bipolar Affective Disorder: Neuroimaging and Neuropathology Findings," Progress in Neuro-Psychopharmacology & Biological Psychiatry, vol. 28, 2004, pp. 943-960.

Hartveit, E. et al., "Brain Stem Modulation of Spatial Receptive Field Properties of Single Cells in the Dorsal Lateral Geniculate Nucleus of the Cat," Journal of Neurophysiology, Oct. 1993, pp. 1644-1655, vol. 70, No. 4.

Hayakawa, Toshiji et al., "Changes in Cerebral Oxygenation and Hemodynamics During Obstructive Sleep Apneas," Chest, vol. 109, pp. 916-921 (1996).

Herwig, U. et al., "Antidepressant Effects of Augmentative Transcranial Magnetic Stimulation," British Journal of Psychiatry, Nov. 2007. pp. 441-448.

Higurashi, Eiji et al., "An Integrated Laser Blood Flowmeter," Journal of Lightwave Technology, vol. 21, No. 3, Mar. 2003, pp. 1-5.

Hilty et al., "A Review of Bipolar Disorder Among Adults," Psychiatric Services vol. 50, 1999, pp. 201-213.

Hodge, Jr., C.J. and Boakye, M., "Biological Plasticity: The Future of Science in Neurosurgery," Neurosurgery, vol. 48, No. 1 (Jan. 2001).

Holmes, A. et al., "Spatiotemporal Dynamics of Error Processing Dysfunctions in Major Depressive Disorder," Arch Gen Psychiatry, vol. 65, No. 2, Feb. 2008, 10 pages.

Hoshi, Yoko et al., "Detection of dynamic changes in cerebral oxygenation coupled to neuronal function during mental work in a man," Neuroscience Letters, vol. 150, pp. 5-8 (1993).

Hoshino et al., "Application of multichannel near-infrared spectroscopic topography to physiological monitoring of the cortex during cortical mapping: technical case report," Surgical Neurology, vol. 64, pp. 272-275 (2005).

Hoskin et al., "Fos expression in the trigeminocervical complex of the cat after stimulation of the superior sagittal sinus is reduced by L-NAME," Neuroscience Letter, 1999, vol. 266, No. 3, pp. 173-176, Elsevier Science, Ireland Ltd.

How Imagent™ Works. ISS Inc., http://www.iss.com-Products-imagent_fmri.html, 1 page [Retrieved on Oct. 14, 2005].

Huang, Ying-Zu et al., "Theta Burst Stimulation of the Human Motor Cortex," Neuron, vol. 45, pp. 201-206 (Jan. 20, 2005).

Huerta et al., "Low-Frequency Stimulation at the Troughts of 0-Oscillation Induces Long-Term Depression of Previously Potentiated CA1 Synapses," Journal of Neurophysiology vol. 75, No. 2, Feb. 1996, pp. 877-884.

Hummel, Friedhelm et al., "Effects of non-invasive cortical stimulation on skilled motor function in chronic stroke," Brain Advance Access, pp. 1-10, (Jan. 5, 2005).

Imagent™ Functional Brain Imaging System, ISS, Inc., http://www.iss.com-Products-imagent.html, 2 pages [Retrieved on Oct. 14, 2005].

Imagent™ functional Near Infrared Imaging System (fNIRS) Brain Imaging Using Infrared Photons, ISS Inc., http://www.iss.com-products-imagent-Imagent.pdf, 8 pages [Retrieved on Oct. 14, 2005].

Ishibashi, Tomoko et al., "Astrocytes Promote Myelination in Response to Electrical Impulses," Neuron 49, pp. 823-832, (Mar. 16, 2006).

Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp. 571-577 (Dec. 2003).

Jimenez et al., "A Patient with a Resistant Major Depression Disorder Treated with Deep Brain Stimulation in the Inferior Peduncle," Neurosurgery, 57(3): 585-593, 2005.

Kauhanen et al., "Domains and Determinants of Quality of Life After Stroke Caused by Brain Infarction," Arch. Phys. Med. Rehabil., vol. 81, pp. 1541-1546 (Dec. 2000).

Keightley et al., "An fMRI study investigating cognitive modulation of brain regions associated with emotional processing of visual stimuli," Neuropsychologia, 41(5): 585-96, 2003.

Johansen-Berg et al., "Anatomical Connectivity of the Subgenual Cngulate Region Targeted with Deep Brain Stimulation for Treatment-Resistant Depression," Cerebral Cortex, 18:1374-1383, Jun. 2008.

Keightley et al., "Personality influences limbic-cortical interactions during sad mood induciton," Neuroimage, 20(4): 2031-9, 2003.

Keller, G. M., "In vitro differentiation of embryonic stem cells," Current Opinion in Cell Biology, Dec. 1995, 7(6):862-869.

Kelly-Spratt, K. "Transfection of PC-12 cells: a model system for primary neuronal cells," Qiagen News, Customer application article, www.qiagen.com, Issue 4, 1998, 2 pages.

Kennedy et al., "Changes in regional barin glucose metabolism measured with positron emission tomography after paroxetine treatment of major depression," Am. J. Psychiatry, 158(6): 899-905, 2001.

Ketter, et al., "Functional Brain Imaging, Limbic Function, and Affective Disorders," The Neuroscientist, vol. 2, No. 1, 1006, pp. 55-65.

Keyvani, Kathy et al., "Suppression of proteasome C2 contralateral to ischemic lesions in rat brain," Brain Research, vol. 858, pp. 386-392, 2000.

Kido, D. et al., "Computed Tomographic Localization of the Precentral Gyrus," Neuroradiology, May 1980, 5 pages.

Kilgard, Michael et al., "Cortical Map Reorganization Enabled by Nucleus Basalis Activity," Science, vol. 279 pp. 1714-1717 (Mar. 13, 1998).

Kimura et al., "Electrically induced neurite outgrowth of PC12 cells on the electrode surface," Med. Biol. Eng. Comput., Jul. 1998, vol. 36, No. 4, pp. 493-498, Springer Berlin / Heidelberg.

Kimura et al., "Gene expression in the electrically stimulated differentiation of PC12 cells," Journal of Biotechnology, Jul. 1998, vol. 63, Issue 1, pp. 55-65, Elsevier.

Kinoshita et al., "Electric cortical stimulation suppresses epileptic and background activities in neocortical epilepsy and mesial temporal lobe epilepsy," Clinical Neurophysiology, vol. 116, 2005, pp. 1291-1299, Elsevier Ireland Ltd.

Kopell et al., "The Continuing Evolution of Psychiatric Neurosurgery," CNS Spectrums, vol. 5, No. 10, pp. 20-31 (Oct. 2000).

Kossoff et al., "Effect of an External Responsive Neurostimulator on Seizures and Electrographic Discharges during Subdural Electrode Monitoring," Epilepsia 45(12):1560-1567, 2004, Blackwell Publishing, Inc.

Koyama et al., "Electrically induced NGF production by astroglial cells," Nature Biotechnology, Feb. 1997, vol. 15, pp. 164-167, 1997 Nature Publishing Group.

Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56:634-639, 2004 Society of Biological Psychiatry.

Lange et al., "Enlarged Amygdala Volume and Reduced Hippocampal Volume in Young Women with Major Depression," Psychological Medicine vol. 34, 2004, pp. 1059-1064.

Larson, John et al., "Reversal of LTP by theta frequency stimulation," Brain Research, 600: pp. 97-102 (1993).

Lazar, M. et al., "White Matter Tractography Using Diffusion Tensor Deflection," Human Brain Mapping, 18:306-321, (2003).

L-DOPA dyskinesias, BioChemistry of PD, http://www.mayo.edu-fdp-pd-info-dyskinesias.htm [Retrieved on Dec. 22, 2005].

Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).

Liepert et al., "Treatment-Induced Cortical Reorganization After Stroke in Humans," Stroke, Jun. 2000, 31(6):1210-1216.

Liotti et al., "The role of functional neuroimaging in the neuropsychology of depression," J. Clin. Exp. Neuropsychol., 23(1): 121-36, 2001.

Liotti et al., "Differential Limbic-Cortical Correlates of Sadness and Anxiety in Healthy Subjects: Implications for Affective Disorders," Society of Biological Psychiatry, vol. 48, 2000, pp. 30-42.

Liotti et al., "Unmasking disease-specific cerebral blood flow abnormalities: mood challenge in patients with remitted unipolar depression," Am. J. Psychiatry, 159(11): 1830-40, 2002.

Little et al., "How Common is Resistance to Treatment in Recurrent, Nonpsychotic Geriatric Depression?", American Journal of Psychiatry 155: Aug. 8, 1998, pp. 1035-1038.

Liu, Rong-Huan et al., "Electrophysiological Properties of Mitogen-Expanded Adult Rat Spinal Cord and Subventricular Zone Neural Precursor Cells," Experimental Neurology, Mar. 1999, pp. 143-154, vol. 158.

Lozano, A. et al., "Subcallosal Cingulate Gyrus Deep Brain Stimulation for Treatment-Resistant Depression," Priority Communication, Notice in the Press, Society of Biological Psychiatry. Copyright 2008, 7 pages.

Lutsep et al., "Safety of Cortical Stimulation in Patients with Hemiparetic Stroke," Oasis, Online Abstract Submission and Invitation System—Program Planner, International Stroke Conference 2005, 1 pages, American Stroke Association.

Malenka, R.C. and Nicoll, R.A., "Long-Term Potenetiation—A Decade of Progress?," Neuroscience, vol. 285, No. 5435, Issue of Sep. 17, 1999, pp. 1870-1874.

Mansur, C.G. et al., "A sham stimulation-controlled trial of rTMS of the unaffected hemisphere in stroke patients," Neurology, vol. 64, pp. 1802-1804 (2005).

Martin et al., "Transcranial Magnetic Stimulation as a Complementary Treatment for Aphasia," Semin Speech Language, vol. 25, pp. 181-191 (2004) Abstract Only—1 page.

Martinez et al., "Motor hand recovery after stroke Prognostic yield of early transcranial magnetic stimulation," Electromyogr. Clin. Neurophysiol., Oct.-Dec. 1999, 39(7):405-410.

Massaro, D.W. and Bosseler, A., "Perceiving Speech by Ear and Eye: Multimodal Integration by Children with Autism," Journal of Developmental and Learning Disorders, vol. 7, 2003, pp. 111-144.

Massaro, D.W. et al., "A Multilingual Embodied Conversational Agent," Hawaii International Conference on System Sciences, 2005, 8 pages.

Massaro, D.W., "Perceiving Talking Faces: From Speech Perception to a Behavioral Principle," MIT Press, 1998, pp. 141-143.

Massaro, D.W., "Symbiotic Value of an Embodied Agent in Language Learning," Hawaii International Conference on System Sciences, 2004, 10 pages.

Mayberg et al., "Cingulate function in depression: a potential predictor of treatment response," Neuroreport, 8(4): 1057-61, 1997.

Mayberg et al., "Clinical correlates of PET- and SPECT-identified defects in dementia," J. Clin Psychiatry, 55 Suppl.: 12-21, 1994.

Mayberg et al., "Deep brain stimulation for treatment-resistant depression," Neuron, 45(5): 651-60, 2005.

Mayberg et al., "Depression in Parkinson's disease: a biochemical and organic viewpoint," Adv. Neurol., 65: 49-60, 1995.

Mayberg et al., "Paralimbic frontal lobe hypometabolism in depression associated with Huntington's disease," Neurology, 42(9): 1791-7, 1992.

Mayberg et al., "Paralimbic hypoperfusion in unipolar depression," J. Nuci. Med., 35(6):929-34, 1994.

Mayberg et al., "Reciprocal Limbic-Cortical Function and Negative Mood: Converging PET Findings in Depression and Normal Sadness," Am. J. Psychiatry 156:May 5, 1999, pp. 675-682.

Mayberg et al., "Regional Metabolic Effects of Fluoxetine in Major Depression: Serial Changes and Relationship to Clinical Response," Biological Psychiatry vol. 48, 2000, pp. 830-843.

Mayberg et al., "Selective hypometalbolism in the inferior frontal lobe in depressed patients with Parkinson's disease," Ann Neurol., 28(1): 57-64, 1990.

Mayberg et al., "The Functional Neuroanatomy of the Placebo Effect," American Journal of Psychiatry vol. 159, 2002, pp. 728-737.

Mayberg, "Depression, II: localization of pathophysiology," Am. J. Psychiatry, 159(12): 1979, 2002.

Mayberg, "Frontal lobe dysfunction in secondary depression," J. Neuropsychiatry Clin. Neurosci., 6(4): 428-42, 1994.

Mayberg, "Position emission tomography imaging in depression: a neural systems perspective," Neuroimaging Clin. N. Am., 13(4): 805-15, 2003.

Mayberg, Helen, "Modulating Dysfunctional Limbic-Cortical Circuits in Depression: towards development of brain-based algorithms for diagnosis and optimised treatment," British Medical Bulletin vol. 65, 2003, pp. 193-207.

Mayberg, Helen, "Modulating Limbic-Cortical Circuits in Depression: Targets of Antidepressant Treatments," Seminars in Clinical Neuropsychiatry vol. 7, No. 4, Oct. 2002, pp. 255-268.

Mayberg, Helen; "Limbic Cortical Dysregulation: A Proposed Model of Depression," Journal of Neuropsychiatry vol. 9 No. 3, 1997, pp. 471-481.

Medtronic, Inc., "Neurostimulator and Their Selection," http://www.medtronic.com/neuro/paintherapies/pain_treatment_ladder/neurostimulation/stimulators_stim_sel/neuro_stim_stim_sel.html, (2001), 6 pgs, Minneapolis, MN.

Mendonca et al., "Directly applied low intensity direct electric current enhances peripheral nerve regeneration in rats," J Neurosci Methods, Oct. 30, 2003, 129(2):183-90.

Meyerson, B.A. et al., "Motor Cortex Stimulation as Treatment of Trigeminal Neuropathic Pain", Acta Neurochirurgica Supplementum, vol. 58, pp. 150-153 (1993).

Mezey, Eva et al., "Comment on 'Failure of Bone Marrow Cells to Transdifferentiate into Neural Cells in Vivo'," Science 299: 1184b-c, Feb. 2003.

Misawa et al., "Low-frequency transcranial magnetic stimulation for epilepsy partialis continua due to cortical dysplasia," Journal of the Neurological Sciences, vol. 234, 2005, pp. 37-39.

Miyakoshi, Junji et al., "Exposure to magnetic field (5 mT at 60 Hz) does not affect cell groth and c-myc gene expression," Journal of Radiation Research, Sep. 1996, pp. 185-191, vol. 37, No. 3, The Japan Radiation Research Society, Chiba, Japan.

Montgomery, "Thalamic Stimulation," Neuroscience Pathways, The Cleveland Clinic Foundation, 2 pages.

Moskowitz, M.D., "Basic Mechanisms in Vascular Headache," Neurologic Clinics, Nov. 1990, vol. 8, No. 4, pp. 801-815.

Motamedi et al., "Optimizing Parameters for Terminating Cortical Afterdischarges with Pulse Stimulation," Epilepsia 43(8):836-846, 2002, Blackwell Publishing, Inc.

Murry, Charles et al., "Hematopietic Stem Cells do not Transdifferentiate into Cardiac Myocytes in Myocardial Infarcts," Nature 428: 664-668, Apr. 2004.

Nakae, H., "Morphological differentiation of rat pheochromocytoma cells (PC12 cells) by electric stimulation," Brain Research, vol. 558, No. 2, Sep. 1991, pp. 348-352, Elsevier Science Publishers B. V.

Netz et al., "Reorganization of motor output in the non-affected hemisphere after stroke," Brain, 120, pp. 1579-1586 (1997).

Nguyen et al., "Chronic motor cortex stimulation in the treatment of central and neuropathic pain. Correlations between clinical, electrophysiological and anatomical data," Pain, Sep. 1999, vol. 82, No. 3, pp. 245-251, Elsevier Science, B.V.

Nitsche, M.A. and Paulus, W., "Excitability changes induced in the human motor cortex by weak transcranial direct current stimulation," The Journal of Physiology, Sep. 15, 2000, 527(3):633-9.

Nitsche, Michael A. et al. "Facilitation of Implicit Motor Learning by Weak Transcranial Direct Current Stimulation of the Primary Motor Cortex in the Human," Journal of Cognitive Neuroscience, May 2003, 15(4):619-26, Published by the MIT Press with the Cognitive Neuroscience Institute.

Nitsche, Michael A. et al., "Level of action of cathodal DC opographyn induced inhibition of the human motor cortex," Dec. 2, 2002, Clinical Neurophysiology 114 (2003) 600-604.

Nudo, Randolph J. et al., "Recovery after damage to motor cortical areas," Current Opinion in Neurobiology, vol. 9, Issue 6, pp. 740-747, Dec. 1, 1999.

Olesen, "Classification and diagnostic criteria for headache disorders, cranial neuralgias and facial pain," Headache classification committee of the International Headache Society, 1988, 12 pages, Norwegian University Press.

Oliveri et al., "Paired transcranial magnetic stimulation protocols reveal a pattern of inhibition and facilitation in the human parietal cortex," The Journal of Physiology, Dec. 1, 2000, 529.2, pp. 461-468.

Ongur, D. et al., "The Organization of Networks within the Orbital and Medial Prefrontal Cortex of Rats, Monkeys, and Humans," Cerebral Cortex, Mar. 2000, vol. 10., pp. 206-219.

Onofrio et al., "Surgical Treatment of Chronic Cluster Headache," Mayo Clin Proc, Jul. 1986, vol. 61. pp. 537-544.

Panchanathan, Sethuraman et al., "Rehabilitation of patients with hemispatial neglect using visual-haptic feedback in Virtual reality environment," http://www.public.asu.edu-~tmcdani-publications.htm, 5 pages [Retrieved on Dec. 22, 2005].

Part IV/The Beural Basis of Cognition, p. 342.

Parton, Dr. Andrew et al., "Spatial Neglect", Advances in Clinical Neuroscience and Rehabilitation, vol. 4, No. 4, pp. 17-18, Sep./Oct. 2004.

Pascual-Leone et al., "Study and Modulation of Human Cortical Excitability With Transcranial Magnetic Stimulation," Journal of Clinical Neurophysiology, Jul. 1998, 15(4):333-43, Published by Lippincott Williams & Wilkins.

Pascual-Leone et al., "Transcranial magnetic stimulation and neuroplasticity," Neuropshychologia, Feb. 1999, 37(2):207-17.

Patterson et al., "Electrostimulation: addiction treatment for the coming millennium," J. Altern. Complement Med., 2(4): 485-91, 1996.

Patterson et al., "Neuro-electric therapy: criticisms of the 1984 Bethlem Study," Br. J. Addict., 84(7): 818, 1989.

Patterson, "Effects of neuro-electric therapy (N.E.T.) in drug addiction: interim report," Bull. Narc. 28(4): 55-62, 1976.

Patterson, "Electrostimulation and opiate withdrawal," Br. J. Psychiatry, 146-213. 1985.

Patterson, "Electrotherapy: addictions and neuroelectric therapy," Nurs. Times, 75(48): 2080-3, 1979.

Paulus, W, "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.

Paulus, Walter, "Toward Establishing a Therapeutic Window for rTMS by Theta Burst Stimulation," Neuron, vol. 45, pp. 181-183 (Jan. 20, 2005).

Pearson, Helen, "Shock tactics for new neurons—Electricity may trigger nerve growth.", http://www.nature.com/nsu/010315/010315-8.html. (Mar. 14, 2001), 2 pgs, Nature News Service, Macmillan Magazines Ltd. 2001.

Penn, Michael, "Stemming Parkinson's," On Wisconsin Alumni Magazine, Summer 2003, http://www.uwalumni.com-onwisconsin-2003_summer-research.html, 1 page [Retrieved on Dec. 22, 2005].

Perceptual Disorders. National Academy of Neuropsychology, Inc., [Retrieved on Sep. 17, 2005]. Retrieved from the internet <URL http://www.nanonline.org/nandistance/mtbi/ClinNeuro/perceptual.html>.

Petrides, M. et al., "Dorsolateral prefrontal cortex: comparative cytoarchitectonic analysis in the human and the macaque brain and corticocortical connection patterns," European Journal of Neuroscience, vol. 1, pp. 1011-1036, 1999.

Phebus et al., "The Non-Peptide NK-1 Receptor Antagonist LY303870 Inhibits Neurogenic Dural Inflammation in Guinea Pigs," Life Sciences, 1997, vol. 60, No. 18, pp. 1553-1561, Elsevier Science.

Philips et al., "Neurobiology of Emotion Persception I: The Neural Basis of Normal Emotion Perception," Bio Psychiatry vol. 54, 2003, pp. 515-528.

Philips et al., "Neurobiology of Emotion Persception II: Implications for Major Psychiatric Disorders," Biol Psychiatry vol. 54, 2003, pp. 515-528.

Pierce, K. et al., "Face Processing Occurs Outside the Fusiform 'Face Area'in Autism: Evidence from Functional MRI," Brain, vol. 124, 2001, pp. 2059-2073.

Pirotte, Benoit, M.D., et al., "The Zeiss-MKM system for frameless image-guided approach in epidural motor cortex stimulation for central neuropathic pain," 2001, vol. 11, pp. 1-6.

Plummer et al., "Assessment of Unilateral Neglect", Physical Therapy Journal, vol. 83, pp. 732-740, 2003.

Politis, M. J., "Mammalian Optic Nerve Regeneration Following the Application of Electric Fields," The Journal of Trauma, Nov. 1988, vol. 28, No. 11, pp. 1548-1552.

Press Release: The Nobel Prize in Physiology or Medicine 1986, Nobelprize.org, http://nobelprize.org/cgi-bin/print?from=%2Fnobel_prizes%2Fmedicine%2Flaureates%2..., pp. 1-5 [internet accessed Dec. 12, 2007].

Price, J. et al., "Neurotransplantation in neurodegenerative disease: a survey of relevant issues in developmental neurobiology," Novartis Foundation Symposium 231, 2000, pp. 148-165, Wiley, Chichester, UK. [Published Online: Sep. 26, 2003].

Quirk, et al., "Stimulation of medial prefrontal cortex decreases the responsiveness of central amygdala output neurons," The Journal of Neuroscience, 2003, 23(25): 8800-8807.

Rajikowska, G. et al., "Cytoarchitectonic Definition of Prefrontal Areas in the Normal Human Cortex: II. Variability in Locations of Area 9 and 46 and Relationship to the Talairach Coordinate System," Cerebral Cortex, Jul./Aug. 1995, pp. 323-337.

Rauch, S. L., "Neuroimaging and Neurocircuitry Models Pertaining to the Neurosurgical Treatment of Psychiatry Disorders," Neurosurg Clin N. Am., vol. 14, 2003, pp. 213-223.

Reinecke, Hans et al., "Skeletal Muscle Stem Cells do not Transdifferentiate into Cardiomyocytes After Cardiac Grafting," J Mol Cell Cardiol 34: 241-249, (2001).

Rezai, "Neurostimulation," Neurological Research, vol. 22, No. 3 pp. 235-273 (Apr. 2000).

Robinson, Kenneth R., "The Responses of Cells to Electrical Fields: A Review," The Journal of Cell Biology, vol. 101, pp. 2023-2027 (Dec. 1985).

Rodegerdts, Enno A. et al., "In Vitro Evaluation of Teratogenic Effects by Time-Varying MR Gradient Fields on Fetal Human Fibroblasts," Journal of Magnetic Resonance Imaging, (2000), pp. 150-156, vol. 12, Wiley-Liss Inc.

Ross, Donald A., M.D., et al., "A Percutaneous Epidural Screw Electrode for Intracranial Electroencephalogram Recordings Technical Note," Neurosurgery, 1993, vol. 33, No. 2, 5 pages.

Ross, Philip E., "The New Physical Therapy," Red Herring, May 2001, pp. 176, 178 and 180.

Rossi et al., "Effects of Repetitive Transcranial Magnetic Stimulation on Movement-related Cortical Activity in Humans," Cerebral Cortex, vol. 10, No. 8, pp. 802-808 (Aug. 2000).

Roux et al., "Chronic Motor Cortex Stimulation for Phantom Limb Pain: A Functional Magnetic Resonance Imagining Study: Technical Cast Report," Neurosurgery, vol. 48, No. 3 (Mar. 2001).

Saitou et al., "Cerebral Blood Volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).

Sander et al., "The Human Amygdala: An Evolved System for Relevance Detection," Reviews in Neuroscience vol. 14, 2003, pp. 303-316.

Sandkuhler, "Learning and memory in pain pathways," Pain, Nov. 2000, 88(2):113-18, Elsevier/North-Holland.

Sanes, "The Relation between Human Brain Activity and Hand Movements," NeuroImage, May 2000, 11(5), pp. 370-374.

Sanes, J. and Donoghue, J.P., "Plasticity and Primary Motor Cortex," Annual Review of Neuroscience, 2000, 23:393-415.

Sato, Kei et al., "Growth of human cultured cells exposed to a non-homogeneous static magnetic field generated by Sm-Co magnets," Biochimica et Biophysica Acta, (1992), pp. 231-238, vol. 1136, Elsevier Science Publishers.

Schaefer, Pamela W. et al., "Assessing Tissue Viability with MR Diffusion and Perfusion Imaging," AJNR, 24: pp. 436-443 (Mar. 2003).

Schaffler, Leonard et al., "Quantative Comparison of Language Deficits Produced by Extraoperative Electrical Stimulation of Broca's, Wernicke's, and Basal Temporal Language Areas" Epilepsia 37(5) (1996) 463-475.

Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).

Schiff et al., "A neuromodulation strategy for rational therapy of complex brain injury states," Neurological Research, vol. 22 pp. 267-272 (Apr. 2000).

Schmidt, E M, et al., "Feasibility of a visual prosthesis for the blind based on intracortical microstimulation of the visual cortex," Brain, Oxford University Press, Oxford, GB, vol. 119, No. part 2, Apr. 1, 1996, pp. 507-522.

Schulz et al., "Localization of Epileptic Auras Induced on Stimulation by Subdural Electrodes," Epilepsia, Dec. 1997, vol. 38, Issue 12, pp. 1321-1329.

SCIRun, Scientific Computing and Imaging Institute. http://www.sofware.sci.utah.edu-scirun.html, 2 pages [Retrieved on Jul. 24, 2005].

Semniowicz et al., "Limbic-frontal Circuitry in Major Depression: A Path Modeling Metanalysis," NeuroImage vol. 22, 2004, pp. 409-418.

Shams, L. et al., "What You See is What You Hear," Nature, vol. 408, 2000, p. 788.

Sheline, Yvette, "3D MRI Studies of Neuroanatomic Changes in Unipolar Major Depression: The Role of Stress and Medical Comorbidity," Biol Psychiatry, vol. 48, 2000, pp. 791-800.

Shimizu et al., "Therapeutic efficacy of transcranial magnetic stimulation for hereditary spinocerebellar degeneration," Tohoku Journal of Experimental Medicine, 189(3):203-11 (Nov. 1999).

Shin, et al., "A Functional Magnetic Resonance Imaging Study of Amygdala and Medial Prefrontal Cortex Responses to Overly Presented Fearful Faces in Posttraumatic Stress Disorder," Arch en Psychiatry, vol. 62, Mar. 2005, 273-281.

Shinohara et al., "Laser Dopler Velocimeter Using the Self-Mixing Effect of a Semiconductor LaserDiode," Applied Optics, vol. 25, No. 9, May 1986, pp. 1417-1419.

Siebner et al., "Lasting cortical activation after repetitive TMS of the motor cortex," Neurology 54, pp. 956-963 (Feb. 2000).

Sioutos et al. Continuous Regional Cerebral Cortical Blood Flow Monitoring in Head-injured Patients, Neurosurgery, vol. 36, No. 5, May 1995, pp. 943-949.

Snowling, M. and Frith, U., "Comprehension in 'Hyperlexic' Readers," Journal of Experimental Child Psychology, vol. 42, 1986, pp. 392-415.

Soares et al., "The Functional Neuroanatomy of Mood Disorders," J. Psychiat. Res., vol. 31, No. 4, 1997, pp. 393-432.

Sobotka, et al., "Can delay-period activity explain working memory?" Journal of Neurophysiolog, vol. 93, No. 1, Jan. 1, 2005, pp. 128-136.

Spencer, P.E. and Marschark, M., "Spoken Language Development of Deaf and Hard-of-Hearing Children," Oxford University Press, 2006, pp. 212-243.

Starkstein et al., "Depression and cognitive impairment in Parkinson's disease," Brain. 112 (Pt. 5) 1141-53, 1989.

Stefan et al., "Induction of plasticity in the human motor cortex by paired associative stimulation," Brain, vol. 123, No. 3, pp. 572-584 (Mar. 2000).

Stefurak et al., "Deep brain stimulation for Parkinson's disease dissociates mood and motor circuits: a functional MRI case study," Mov. Disord., 18(12): 1508-16, 2003.

Storer et al., "Microiontophoretic application of serotonin (5HT)1B/1D agonists inhibits trigeminal cell firing in the cat," Brain, 1997, vol. 120, Issue 12, pp. 2171-2177, Oxford University Press.

Strangman, Gary et al., "A Quantitative Comparison of Simultaneous BOLD fMRI and NIRS Recordings during Functional Brain Activation," NeuroImage, vol. 17, pp. 719-731 (2002).

Strangman, Gary et al., "Factors affecting the accuracy of near-infrared spectroscopy concentration calculations for focal changes in oxygenation parameters," NeuroImage, vol. 18, pp. 865-879 (2003).

Strangman, Gary et al., "Non-Invasive Neuroimaging Using Near-Infrared Light," Biological Psychiatry, vol. 52, pp. 679-693 (2002).

Strassman et al., "Sensitization of meningeal sensory neurons and the origin of headaches," Letters to Nature, Nature 384, Dec. 1996, pp. 560-564.

Sirens, Lucy et al., "The Ipsilateral Human Motor Cortex Can Functionally Compensate for Acute Contralateral Motor Cortex Dysfunction," Current Biology, vol. 13, pp. 1201-1205 (Jul. 15, 2003).

Suzuki et al., "Selective Electrical Stimulation of Postganglionic Cerebrovascular Parasympathetic Nerve Fibers Originating from the Sphenopalatine Ganglion Enhances Cortical Blood Flow in the Rat," Journal of Cerebral Blood Flow and Metabolism, May 1990, 10(3):383-91.

Taga, Gentaro et al., "Brain imaging in awake infants by near-infrared optical topogrpahy," PNAS, vol. 100, No. 19, pp. 10722-10727 (Sep. 16, 2003).

Tager-Flusberg, H., "A Psychological Approach to Understanding the Social and Language Impairments in Autism," For International Review of Psychiatry, manuscript revised Jun. 14, 1999, 37 pages.

Tang, Cha-Min et al., "Optical Coherence Tomography of the Human Basal Ganglion," Deep Brain Stimulation Consortium Meeting Program Book, Sep. 29-30, 2003, Washington DC.

Taub et al., Chronic Electrical stimulation of the gasserian ganglion for the relief of pain in the series of 34 patients, J. Neurosurg., Feb. 1997, 86(2):197-202.

Temple, "Stem cell plasticity—building the brain of our dreams," Perspectives, Nature Reviews—Neuroscience vol. 2, Jul. 2001, pp. 513-520.

The GES 250 for Dense-Array EEG Research, Electrical Geodesics, Inc., http://www.egi.com/ges250r_n.html, 3 pages [Retrieved on Aug. 25, 2005].

The INVOS Cerebral Oximeter, Somanetics, http://www.somanetics.net/invos.htm, 1 page [retrieved from the internet on Dec. 22, 2005].

The National Institutes of Health (NIH) Consensus Development Program, "Surgery for Epilepsy," National Institutes of Health Consensus Development conference Statement, Mar. 19-21, 1990, 16 pages.

Theoret, Hugo et al., "Exploring Paradoxical Functional Facilitation with TMS," Supplements to Clinical Neurophysiology, vol. 56, pp. 211-219 (2003).

Thomas, Carmen et al., "Do Children with aggressive behavior have temporal lobe changes?" Alasbimn Journal, Year 5, No. 19, 8 pages (Jan. 2003).

Timmermann, Lars et al., "The cerebral oscillatory network of parkinsonian resting tremor," Brain, vol. 126, pp. 199-212, (2003).

Toronov, Vlad et al., "Near-infrared study of fluctuations in cerebral hemodynamics during rest and motor stimulation: Temporal analysis and spatial mapping," Medical Physics, vol. 27, No. 4, pp. 801-815 (Apr. 2000).

Tractography, Absolute Astronomy Reference, http://www.absoluteastronomy.com-encyclopedia-T-Tr-Tractography.htm, 2 pages [Retrieved on Jul. 24, 2005].

Tsubokawa, T. et al., "Chronic Motor Cortex Stimulation for the Treatment of Central Pain," Acta Neurochirurgica, Supplementum. vol. 52, pp. 137-139 (1991).

Tsubokawa, T. et al., "Chronic Motor Cortex Stimulation in Patients with Thalamic Pain," J. Neurosurg 78:393-401, (Mar. 1993).

Tsubokawa, T. et al., "Treatment of Thalamic Pain by Chronic Motor Cortex Stimulation", PACE, vol. 14, pp. 131-134 (Jan. 1991).

Tuch, D. et al., "Conductivity Tensor Mapping of the Human Brain Using Diffusion Tensor MRI," Neurobiology, vol. 98 No. 20, pp. 11697-11701 (Sep. 25, 2001).

Turton et al., "Contralateral and ipsilateral EMG responses to transcranial magnetic stimulation during recovery of arm and hand function after stroke," Electroencephalography and Clinical Neurophysiology, Aug. 1996, 101(4):316-28, Elsevier.

Turton, A. and Lemon, R.N., "The contribution of fast corticospinal input to the voluntary activation of proximal muscles in normal subjects and in stroke patients," Exp. Brain Res., Dec. 1999, 129(4):559-572, Springer Berlin / Heidelberg.

Tyler et al., "Audiological Rehabilitaion of the Tinnitus Client," Journal of The Academy of Rehabilitative Audiology, XXII pp. 30-42 (1989).

Van Der Lee et al., "The Intra- and Interrater Reliability of the Action Research Arm Test: A Practical Test of Upper Extremity Function in Patients With Stroke," Arch. Phys. Med. Rehabil., vol. 82 pp. 14-19 (Jan. 2001).

Van Inzen, Wouter G. et al., "Neuronal differentiation of embryonic stem cells," Biochimica et Biophysica Acta, (1996), pp. 21-26, vol. 1312, Elsevier Science.

Van Kooten, et al., "Neurons in the Fusiform Gyrus are Fewer and Smaller in Autism" Brain, Mar. 10, 2008.

Vanderkooy et al., "Resolution Below the Least Significant Bit in Digital Systems with Dither," JAES, Mar. 1984, vol. 32, No. 3, pp. 106-113.

Velasco et al. "Absolute and Relative Predictor Values of Some Non-Invasive and Invasive Studies for the Outcome of Anterior Temporal Lobectormy," Science Direct, vol. 31, Issue 1, Jan.-Feb. 2000, pp. 62-74, Elsevier Science, Inc.

Velasco et al., "Acute and Chronic Electrical Stimulation of the Centromedian Thalamic Nucleus: Modulation of Reticulo-Cortical Systems and Predictor Factors for Generalized Seizure Control," Archives of Medical Research, May-Jun. 2000, 31(3):304-315, Elsevier Science, Inc.

Velasco et al., "Electrical Stimulation for Epilepsy: Stimulation of Hippocampal Foci," Proceedings of the 13th Meeting of the World Society for Stereotactic and Functional Neurosurgery, Sep. 11-14, 2001, Stereotactic and Functional Neurosurgery, vol. 77, No. 1-4, 2001, pp. 223-227.

Velasco et al., "Neurobiological Background for Performing Surgical Intervention in the Inferior Thalmic Peduncle for Treatment of Major Depression Disorders," Neurosurgery, 57(3): 439-448, 2005.

Velasco et al., "Subacute and Chronic Electrical Stimulation of the Hippocampus on Intractable Temporal Lobe Seizures: Preliminary Report," Archives of Medical Research, May-Jun. 2000, 31(3):316-28, Elsevier Science.

Velasco et al., "Subacute Electrical Stimulation of the Hippocampus Blocks Intractable Temporal Lobe Seizures and Paroxysmal EEG Activities," Epilepsia, Feb. 2000, 41(2):158-169, Lippincott Williams & Wilkins, Philadelphia.

Velasco, et al., "Electrocortical and Behavioral Responses Produced by Acute Electrical Stimulation of the Human Centromedian Thalamic Nuclesu," Electroencephalography and Clinical Neurophysiology, 102: 461-471 (1996).

Videbech et al., "Hippocampal Volume and Drepression: A Meta-Analysis of MRI Studies," Am. J. Psychiatry vol. 161, No. 11, Nov. 2004, pp. 1957-1966.

Viktora, L. et al., "Effect of Prolonged Exposure to a Magnetic Field on the Haematopoietic Stem Cell," Physiologia Bohemoslovaca, (1976), pp. 359-364, vol. 25, vol. 4., Institute of Haematology and Blood Transfusion, Prague.

Violentyev, A. et al., "Touch-Induced Visual Illusion," NeuroReport, vol. 16, No. 10, 2005, pp. 1107-1110.

Volz, K. et al., "Why am I unsure? Internal and external attributions of uncertainty dissociated by fMRI," NeuroImage 21 (2004), pp. 848-847.

Walker-Batson et al., "Amphetamine Paired With Physical Therapy Accelerates Motor Recovery After Stroke," Stroke, vol. 26, No. 12, pp. 2254-2259 (1995).

Waxman et al., "The Interictal Behavior Syndrome of Temporal Lobe Epilepsy," Arch Gen Psychiatry, vol. 32, Dec. 1975, pp. 1580-1586.

Weinand et al., "Cerebral blood flow and temporal lobe epileptogenicity," J Neurosurg, vol. 86, Feb. 1997, pp. 226-232.

Weinand et al., "Cerebral blood flow and temporal lobe epileptogenicity," Neurosurgical Focus, Nov. 1996, vol. 1, No. 5, AANS.ORG, http://www.aans.org/education/journal/neurosurgical/nov96/1-5-3.asp, 17 pages.

Weinand et al., Long-term ictal monitoring with subdural strip electrodes: prognostic factors for selecting temporal lobectomy candidates, J Neurosurg, vol. 77, 1992, pp. 20-28.

Weinand et al., "Surface cortical cerebral blood flow monitoring and single photon emission computed tomography: prognostic factors for selecting temportal lobectormy candidates," Seizure, vol. 3, 1994, pp. 55-59.

Weinand et al., "Targeted Subthreshold Cortical Stimulation for Recovery of Motor Hand Function following Hemiparetic Stroke," Abstract: Apr. 18, 2005, AANS.org, http://www.aans.org/Library/Article.aspx?ArticleId=24934, 2 pages.

Weinand, Martin E. et al., "Cerebral blood flow and temporal lobe epileptogenicity," Retrieved from the Internet on Dec. 22, 2005, http://www.aans.org/education/journal/neurosurgical/nov96/1-5-3.asp, 13 pages.

Weissmen et al., "Cross-National Epidemiology of Major Depression and Bipolar Disorder," JAMA vol. 276, No. 4, Jul. 24/31, 1996, pp. 293-299.

Williams, J.H.G. et al., "Imitation, Mirror Neurons and Autism," to appear in Neuroscience and Behavioral Reviews, 28 pages.

Williams, J.H.G. et al., "Visual-Auditory Integration During Speech Imitation in Autism," Research in Developmental Disabilities, vol. 25, 2004, pp. 559-575.

Woodbury, D. et al., "Adult Rat and Human Bone Marrow Stromal Cells Differentiate Into Neurons," Journal of Neuroscience Research, Aug. 15, 2000, 61(4):364-70, Wiley Interscience, New York, NY.

Yamada, Masahisa et al., "Electrical Stimulation Modulates Fate Determination of Differentiating Embryonic Stem Cells," Stem Cells 25: 562-570 (2007).

Yamamoto et al., "Low-frequency Electric Cortical Stimulation Has an Inhibitory Effect on Epileptic Focus in Mesial Temporal Lobe Epilepsy," Epilepsia, vol. 43, No. 5, 2002, pp. 291-295, Blackwell Publishing, Inc.

Yokoh, Arika et al., "Intermittent versus continuous brain retraction," Journal of Neurosurgery, vol. 58, pp. 918-923 (Jun. 1983).

Young, R.F., "Electrical stimulation of the trigeminal nerve root for the treatment of chronic facial pain," J. Neurosurg., Jul. 1995, 83(1):72-78.

Ziemann et al., "Modulation of Plasticity in Human Motor Cortex after Forearm Ischemic Nerve Block," The Journal of Neuroscience 18(3):1115-1123 (Feb. 1998).

Zilbovicius, M. et al., "Austim: Neuroimaging," Rev Bras Psiquiatr,vol. 28, 2006, pp. S21-S28.

Zilbovicius, M. et al., "Temporal Lobe Dysfunction in Childhood Autism: A PET Study," Am J Psychiatry, 157:12, 2000, pp. 1988-1993.

Australian Examiners Report for Application No. 2003295349; Northstar Neuroscience, Inc.; Dec. 2007; 3 pgs; Australian Patent Office.

European Search Report for Patent Application No. 03786531.8; Northstar Neuroscienc, Inc.; May 6, 2008; 6 pgs; European Patent Office.

EPO Report on Substantive Examination; EPO Patent Application No. 06020759.4; Applicant: Northstar Neuroscience, Inc.; Mailed on Sep. 2, 2008.

EPO, Supplementary Partial European Search Report for EP06836401 dated Oct. 14, 2009.

International Search Report for Application No. PCT/US2002/07077; Applicant: Vertis Neuroscience, Inc., Oct. 22, 2002, 7 pgs.

Written Opinion for PCT/US2002/07077; Jul. 2003; Applicant: Vertis Neuroscience, Inc. (4 pgs).
International Search Report for PCT/US2002/31112; Dec. 2002; Applicant: Vertis Neuroscience, Inc. (7 pgs).
Written Opinion for PCT/US2002/31112; Aug. 2003; Applicant: Vertis Neuroscience, Inc. (5 pgs).
International Search Report for PCT/US2002/31127; Jul. 2003; Applicant: Vertis Neuroscience, Inc. (3 pgs).
Written Opinion for PCT/US2002/31127; May 2003; Applicant: Vertis Neuroscience, Inc. (2 pgs).
International Search Report for PCT/US2002/31128; Sep. 2002; Applicant: Vertis Neuroscience, Inc. (6 pgs).
International Search Report for Application No. PCT/US2002/32695; Applicant: Vertis Neuroscience, Inc.; Dec. 27, 2002; 9 pgs; European Patent Office.
Written Opinion for PCT/US2002/32695; Jun. 2003; Applicant: Vertis Neuroscience, Inc. (2 pgs).
International Search Report and Written Opinion for PCT/US2003/32599; Filed Oct. 15, 2003; Applicant: Northstar Neuroscience, Inc. (7 pages).
International Search Report for PCT/US2003/03678; Jul. 2003; Applicant: Northstar Neuroscience, Inc. (4 pgs).
International Search Report for PCT/US2003/09211 dated Sep. 28, 2005.
Written Opinion for PCT/US2003/03678; Dec. 2003; Applicant: Northstar Neuroscience, Inc. (4 pgs).
International Search Report for PCT/US2003/37855 dated Apr. 29, 2004.
International Search Report for PCT/US2003/39077; May 2004; Applicant: Northstar Neuroscience, Inc. (3 pgs).
International Search Report for PCT/US2003/39078; May 2004; Applicant: North Star Neuroscience, Inc. (5 pgs).
International Search Report for Application No. PCT/US2004/20786; Applicant Northstar Neuroscience, Inc., Jan. 18, 2005, 8 pgs.
International Search Report and Written Opinion for PCT/US2005/24768 dated Aug. 24, 2006.
International Search Report for PCT/US2006/007182 dated Jun. 17, 2008.
International Search Report for PCT/US2006/040908 dated Sep. 25, 2007.
International Search Report for PCT/US2007/075129 dated Sep. 28, 2008.
International Search Report and Written Opinion for PCT/US2008/059645 dated Jul. 17, 2008.
International Search Report for PCT/US2008/060739 dated Sep. 8, 2008.
International Search Report for PCT/US2008/085973 dated Dec. 8, 2008.
International Search Report for PCT/US2009/039032 dated Feb. 20, 2010.

* cited by examiner

TECHNIQUES FOR SELECTING SIGNAL DELIVERY SITES AND OTHER PARAMETERS FOR TREATING DEPRESSION AND OTHER NEUROLOGICAL DISORDERS, AND ASSOCIATED SYSTEMS AND METHODS

CROSS-REFERENCE TO RELATED APPLICATION

The present application claims priority to U.S. Provisional Application 61/086,199, filed Aug. 5, 2008 and incorporated herein by reference.

TECHNICAL FIELD

Aspects of the present disclosure are directed generally toward techniques for selecting signal delivery sites and other signal delivery parameters for treating depression and other neurological disorders, and associated systems and methods.

BACKGROUND

A wide variety of mental and physical processes are controlled or influenced by neural activity in particular regions of the brain. For example, the neural functions in some areas of the brain (i.e., the sensory and motor cortices) are organized according to physical or cognitive functions. Several areas of the brain appear to have distinct functions in most individuals. In the majority of people, for example, the areas of the occipital lobes relate to vision, the regions of the left inferior frontal lobes relate to language, and particular regions of the cerebral cortex appear to be consistently involved with conscious awareness, memory, and intellect.

Many problems or abnormalities can be caused by damage, disease and/or disorders in the brain. Disorders include neuropsychiatric and/or neuropsychological disorders, such as major depression. A person's neuropsychiatric responses may be controlled by a looped signal path between cortical structures, e.g., superficial structures at the prefrontal cortex of the brain, and deeper neural populations.

Neurological problems or abnormalities are often related to electrical and/or chemical activity in the brain. Neural activity is governed by electrical impulses or "action potentials" generated in neurons and propagated along synaptically connected neurons. When a neuron is in a quiescent state, it is polarized negatively and exhibits a resting membrane potential typically between −70 and −60 mV. Through chemical connections known as synapses, any given neuron receives excitatory and inhibitory input signals or stimuli from other neurons. A neuron integrates the excitatory and inhibitory input signals it receives, and generates or fires an action potential when the integration exceeds a threshold potential. A neural firing threshold, for example, may be approximately −55 mV.

When electrical activity levels at either the superficial cortical structure or the deep brain structure are irregular, action potentials may not be generated in the normal manner. For example, action potentials may be generated too frequently, or not frequently enough. Such irregularities can result in a neuropsychiatric disorder. It follows, then, that neural activity in the brain can be influenced by electrical energy supplied from an external source, such as a waveform generator. Various neural functions can be promoted or disrupted by applying an electrical current to the cortex or other region of the brain. As a result, researchers have attempted to treat physical damage, disease and disorders in the brain using electrical or magnetic stimulation signals to control or affect brain functions.

Transcranial electrical stimulation (TES) is one such approach that involves placing an electrode on the exterior of the scalp and delivering an electrical current to the brain through the scalp and skull. Another treatment approach, transcranial magnetic stimulation (TMS), involves producing a magnetic field adjacent to the exterior of the scalp over an area of the cortex. Yet another treatment approach involves direct electrical stimulation of neural tissue using implanted deep brain stimulation electrodes (DBS). However, the foregoing techniques may not consistently produce the desired effect with the desired low impact on the patient. For example, TES may require high currents to be effective, which may cause unwanted patient sensations and/or pain. TMS may not be precise enough to target only specific areas of the brain. Deep brain stimulation is a relatively invasive procedure, and it can be relatively difficult to implant DBS electrodes in tissue located well below the cortex. Accordingly, there exists a need for providing more effective, less invasive treatments for neuropsychiatric and neuropsychological disorders.

DETAILED DESCRIPTION

Introduction

The present disclosure is directed to methods for treating neurologic dysfunction, which may include neuropsychiatric, neuropsychological, neurodevelopmental and/or other disorders, and associated systems for carrying out such methods. As used herein, the phrase "neurologic dysfunction" is used to encompass a variety of conditions or disorders, including neuropsychiatric disorders and neuropsychological disorders. As a further shorthand, the term "neuropsychiatric disorders" is used to include both neuropsychiatric disorders and neuropsychological disorders. Representative types of disorders falling within this definition include major depression, mania and other mood disorders, bipolar disorder, obsessive-compulsive disorder (OCD), Tourette's syndrome, schizophrenia, dissociative disorders, anxiety disorders, phobic disorders, post-traumatic stress disorder (PTSD), borderline personality disorder, as well as others such as Attention Deficit/Hyperactivity Disorder (ADHD) and/or craving or reward driven behaviors (e.g., associated with an addiction to legal or illegal drugs, gambling, sex, or another condition such as obesity).

In general, various aspects of the methods and systems disclosed herein are directed to treating neurological conditions or states with electromagnetic stimulation, typically electrical stimulation applied to particular cortical structures of the patient's brain, e.g., from an epidural or subdural location. As used herein, "stimulation" refers generally to extrinsic signals directed to the patient to achieve a beneficial result. The signals may have an inhibitory or excitatory effect on particular neural populations. One representative technique includes using at least two sets of imaging information to more particularly identify the neural population to which therapeutic electromagnetic signals are delivered. Another particular method, directed to depressed patients, can include applying electromagnetic signals to one or more patient brain regions expected to correspond to the dorsolateral prefrontal cortex (DLPFC) and identifying a change in a region of the brain other than the DLPFC. Based at least in part upon this information, a practitioner can determine whether or not the patient is a candidate for cortical signal delivery to address depression, and/or the practitioner can select a target neural population to receive cortical signals, and/or the practitioner can update cortical signal delivery parameters. Further particular embodiments are described in greater detail below with reference to FIGS. 1-8C.

Figure 1:
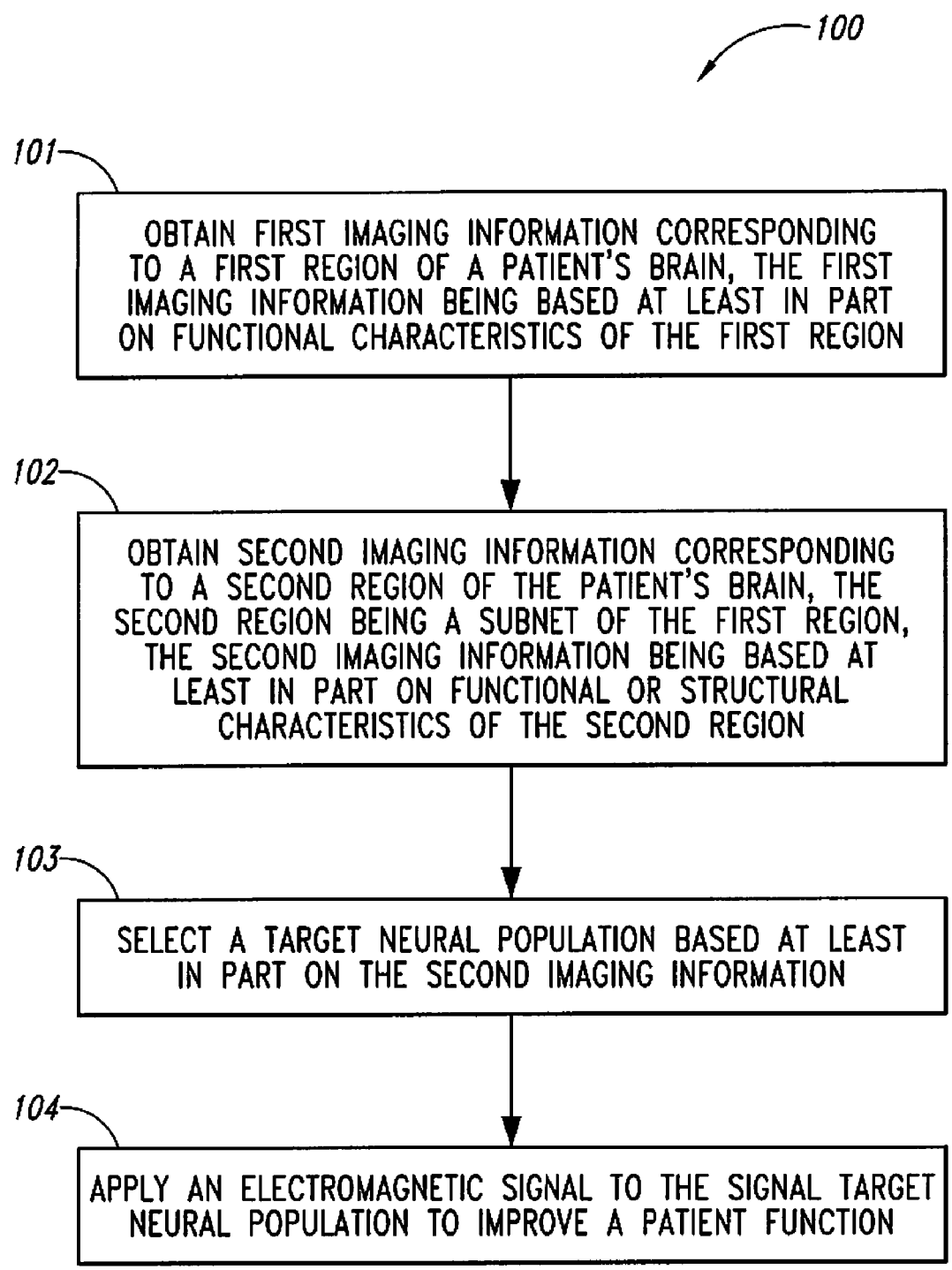
FIG. 1 is a flow diagram illustrating a method for treating a patient in accordance with a particular embodiment of the disclosure.

Systems and Methods for Patient Selection, Target Neural Population Selection, and Signal Delivery Selection FIG. 1 is a flow diagram illustrating a process 100 for treating a patient in accordance with a particular embodiment of the disclosure. The process 100 includes obtaining first imaging information corresponding to a first region of a patient's brain, with the first imaging information being based at least in part on functional characteristics of the first region (process portion 101). For example, the first imaging information can be obtained using functional magnetic resonance imaging (fMRI) techniques. Process portion 102 can include obtaining second imaging information corresponding to a second region of the patient's brain, with the second region being a subset of the first region. The second imaging information can be based at least in part on functional or structural characteristics of the second region, and can have a resolution greater than that of the first imaging information. Accordingly, the second information can be used to more precisely identify a target neural population that will receive therapeutic electromagnetic signals. For example, a typical fMRI-based process for locating a target neural population has a resolution of about 1-3 centimeters. By adding the second information, (e.g., using diffusion tensor imaging processes described later) the practitioner can achieve a resolution of 3 millimeters or less. In addition to increased resolution, the foregoing technique can be conducted without a surgical procedure and is therefore less invasive than other techniques. Still further, this technique can be readily used to identify target neural populations of "silent" neurons, e.g., cognitive, emotive and/or other neurons that typically do not produce an immediate motor or sensory response.

The practitioner can use the first and/or second information to identify particular areas of interest, and/or to eliminate from further consideration areas that are not of interest. In any of these cases, process portion 103 includes selecting a target neural population based at least in part on the second imaging information, and process portion 104 includes applying an electromagnetic signal to the target neural population to improve a patient function. For example, this technique can be used to improve the functioning of a patient suffering from depression. A representative example is described in further detail below with reference to FIG. 2.

Figure 2:
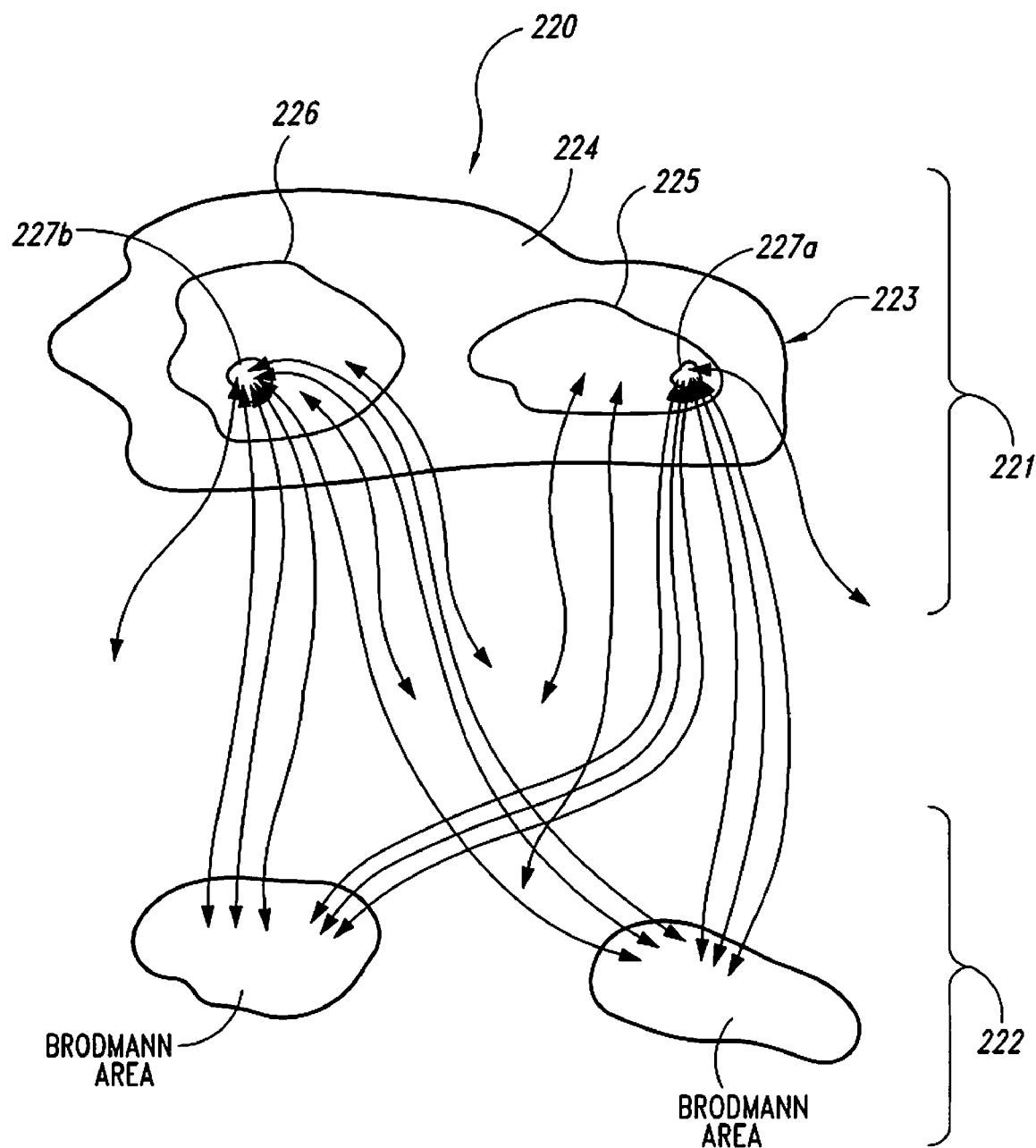
FIG. 2 is a schematic illustration of cortical and sub-cortical brain structures, along with regions selected in accordance with embodiments of the disclosure.

FIG. 2 is a schematic illustration of a patient's brain 220 illustrating cortical structures 221 (e.g., superficial or outer structures) located at the cortex 223, and sub-cortical structures 222 (e.g., deeper, non-superficial structures) located below or within the cortex 223. The cortical structures 221 can include the dorsolateral prefrontal cortex (DLPFC) 224 which has neuronal tracts (illustrated schematically by doubled-headed arrows in FIG. 2) extending to the sub-cortical structures 222. The DLPFC has connections with many sub-cortical structures 222 but for purposes of illustration, Brodmann area 10 and Brodmann area 25 are specifically shown in FIG. 2. In a particular embodiment, the practitioner can preferentially focus imaging tasks on one or brain locations expected to form a portion of or correspond to the DLPFC and then preferentially direct electromagnetic signals to portions of the DLPFC. In other embodiments, the practitioner can focus imaging tasks (and electromagnetic signals) on particular neuroanatomical structures, portions of which may be included in the DLPFC, e.g., portions of the patient's middle frontal gyrus, and/or superior frontal gyrus. In still further embodiments, the practitioner can focus imaging tasks (and/or electromagnetic signals) on still other structures, e.g., the patient's inferior frontal gyrus, orbitofrontal cortex, and/or ventrolateral prefrontal cortex. Additional details of techniques for targeting and applying therapy to these structures are included in pending U.S. application Ser. No. 12/330,437, filed Dec. 8, 2008 and incorporated herein by reference.

The DLPFC 224 can include subareas, for example, a cognitive area 225 associated with the patient's cognitive functioning, and an emotive area 226 associated with the patient's emotional functioning, both shown schematically in FIG. 2. The locations of these areas may in at least some cases vary from patient to patient. In addition, individual patients may have a depression condition that results from dysfunctions in the cognitive area 225 or the emotive area 226 or both the cognitive area 225 and the emotive area 226. Using functional imaging techniques (e.g., fMRI), a practitioner can identify which of the two areas is a likely candidate for cortical stimulation. For example, the patient can be exposed to a stimulus (described in further detail later) that triggers an acute depression response, while the patient's brain is imaged. In some cases, only one of the areas 225, 226 may be a suitable candidate, and in other embodiments, both areas may be suitable candidates. In any of these cases, the cognitive area 225 and/or the emotive area 226 can correspond to the first region of the patient's brain described above with reference to FIG. 1. In still another embodiment, neither the cognitive area 225 nor the emotive area 226 may particularly stand out when the first imaging information is obtained, and accordingly, the entire DLPFC 224 or some other region of the DLPFC may correspond to the first region described above with reference to FIG. 1.

As shown in FIG. 2, the cognitive area 225 and the emotive area 226 may each have many tracts that descend to a variety of sub-cortical structures 222. In certain embodiments, the practitioner may be particularly interested in applying electrical signals to those areas of the DLPFC 224 that have a significant number of neuronal fibers or tracts that descend to Brodmann area 10 and/or Brodmann area 25. Accordingly, the practitioner can obtain the second imaging information described above with reference to FIG. 1 to identify a second, more precisely defined region of the patient's brain suitable for receiving cortical stimulation. For example, if the cognitive area 225 is of particular interest, the second imaging information can be used to identify a second region 227a that includes tracts (or a greater number of tracts or density of tracts) extending to Brodmann area 25 and/or Brodmann area 10. If the emotive area 226 is of particular interest, the practitioner can identify a second region 227b that has tracts (or a greater number of tracts or density of tracts) descending to Brodmann area 25 and/or Brodmann area 10. Accordingly, the first imaging information described above with reference to FIG. 1 can identify a general region for cortical stimulation with a first level of resolution, and the second imaging information can identify one or more second regions with a higher level of resolution to more precisely identify one or more target neural populations. Further details of suitable techniques for obtaining the first imaging information and the second imaging information are described below.

In at least some embodiments, the first imaging information is based at least in part on functional characteristics of the first region. For example, the first information can be obtained using correlates that are associated with or indicative of neural functioning levels. Such correlates include blood flow, metabolism, perfusion, glucose levels, water levels, magnetic characteristics, and/or electrical characteristics. Suitable techniques for identifying and/or measuring such correlates can include fMRI, spectroscopy based on MRI, positron emission tomography (PET), single photon emission computed tomography (SPECT), and/or computed tomography (CT). In any of these embodiments, the image or information used to produce the image is correlated with a particular activity related to the patient's depression. For example, in some cases, the patient's working memory is affected by depression and accordingly, the patient can undertake working memory tasks while the first imaging information is collected. In other embodiments, the patient can be exposed to emotion-triggering stimuli (e.g., visual, auditory, tactile and/or olfactory stimuli) so as to identify regions of the brain that are active in response to such stimuli and are correlated with the patient's depression. Further details associated with assessing patient functioning are included in co-pending U.S. Patent Publication No. US 2008/0103548, incorporated herein by reference.

The second imaging information can be structural or functional in nature and is generally obtained for a smaller region of the brain (e.g., a subset of the first region) than is the first imaging information. In a particular embodiment, diffusion tensor imaging (DTI) techniques are used to identify neuronal tracts or fibers descending to sub-cortical areas that are known or expected to play a role in the patient's depression. More specifically, the practitioner can identify a "seed point" at the DLPFC using the first information. On the basis of the seed point, the practitioner can perform a fiber tracking analysis to identify fibers that connect the DLPFC to specific sub-cortical structures. This technique can be performed for multiple seed points at the DLPFC, and one or more target neural populations can be selected to include the areas of the DLPFC having the highest density of (intact) fiber tracts that descend to the specific sub-cortical area(s) of interest. Accordingly, the foregoing tractography analysis can apply to white matter in the brain, in contrast to techniques that may apply only to gray matter.

The foregoing approach is expected to produce better (e.g., more efficacious) results than identifying and stimulating a deep brain structure because many deep brain structures have a high density of tracts that extend to many different superficial locations, some of which may be associated with the patient's depression, and many of which are not. As a result, methods that focus on stimulating deep brain areas may be inefficient and/or may create unintended cortical effects because it may be difficult to accurately target the deep brain area(s) of particular interest. Accordingly, in particular embodiments of the present techniques, no deep brain stimulation is applied. In a further particular aspect of this embodiment, simulation is applied only to areas identified based on the second imaging information. Further information relating to the use of DTI for site identification is included in U.S. Patent Publication No. US 2008/0039895, incorporated herein by reference.

In general terms, DTI techniques identify neuronal tracts by identifying adjacent tissue volumes (voxels) having diffusion tensors aligned in the same direction. In addition to or in lieu of using diffusion characteristics to identify tracts, the practitioner can use diffusion information to identify the level of anisotropy of the brain tissue, typically referred to as fractional anisotropy (FA). In general terms, FA refers to the magnitude of the diffusion tensor, as opposed to its direction. It is expected that in at least some embodiments, the level of anisotropy can be indicative of regions affected by depression. For example, if the FA level for a particular region of the DLPFC is relatively low (e.g., lower than a standard or average value across a general patient population), this can indicate an area associated with the patient's depression. If the FA level is low, yet still above a threshold value, this may indicate an area suitable for cortical stimulation. Accordingly, the FA level can be used to identify patients who are suitable candidates for cortical stimulation therapy, and/or target neural populations in patients who are suitable candidates. Suitable threshold FA values are expected to be different for different brain areas and/or different neuropsychiatric/neuropsychological conditions. FA values may also be used to identify changes (e.g., improvements) in patient condition over time, as a result of the therapeutic treatments described herein. For example, it is expected that the patient's FA values may increase as a result of structural changes, including but not limited to dendritic sprouting and/or the formation of new axons.

In other embodiments, functional characteristics of the brain may be used to identify the second region described above with reference to FIG. 1. For example, spectroscopy may be used. In a particular aspect of this embodiment, the practitioner can analyze fMRI results on a real-time or nearly real-time basis, and conduct a magnetic resonance spectroscopy (MRS) diagnosis on a subset region of the brain in a single patient visit. When the practitioner uses spectroscopy to obtain the second information, the practitioner can focus the analysis on a smaller area than may be used to obtain the first information, resulting in a higher sensitivity analysis and an expected increase in the precision of the results.

Techniques other than spectroscopy may also be used to identify the second brain region, based on structural characteristics of the brain. For example, the thickness of the gray matter within the first region can be used to identify the second region. In a particular embodiment, the gray matter thickness is assessed using MRI techniques. In general, the greater the gray matter thickness, the greater the functionality of the tissue. The practitioner can select highly functional tissue as the target neural population in cases for which it is expected that this will be beneficial, e.g., when it is expected that stimulation will encourage the functional tissue to take on additional functionality. The practitioner can select less functional tissue in cases for which it is expected that stimulation can raise the functionality to normal or approximately normal levels. These techniques can be used separately or in combination.

As described above with reference to FIG. 1, once a suitable second region has been selected, the practitioner can apply an electromagnetic signal to the target neural population to improve a patient function. In a particular embodiment, the practitioner uses a cortical electrode (e.g., an electrode positioned epidurally or subdurally within the cranial cavity of the patient's skull, proximate to the target neural population, and outside a cortical surface of the patient's brain) to apply electrical signals to the target neural population. Depending upon the patient's condition, the electromagnetic signals may be applied in a manner that inhibits the target neural population, or excites or facilitates the target neural population. The frequency and/or polarity (anodal or cathodal) of the signal may be selected to achieve the desired result. The stimulation may be delivered so as to have a direct effect on the target neural population, for example, an effect that lasts as long as or slightly longer than the stimulation itself. In other embodiments, the stimulation may be applied to neural populations that are expected to retain long-lasting changes (e.g., neuroplastic changes) that can last for days, weeks, months or years after the stimulation has ceased. In such cases, the treatment regimen can include an adjunctive therapy in combination with the electrical stimulation. Representative adjunctive therapies include working memory tasks, exposure to emotional triggers, psychological counseling and others.

In other embodiments, techniques generally similar to the foregoing techniques can be used to perform functions other than identifying suitable target neural populations. For example, such techniques can be used to screen treatment candidates. In a particular embodiment, if the patient's FA level is low, the patient may be a suitable candidate for cortical stimulation treatment. However, if the FA level is too low, the patient may not respond adequately to cortical stimulation and may accordingly be screened out or selected for an alternative treatment.

In another embodiment, one or more of the foregoing techniques can be used to select a particular treatment modality. For example, if the patient's FA value is within a particular range, the patient may be selected to undergo cortical stimulation. If the FA value is within a different range, the patient may be expected to respond better to transcranial magnetic stimulation (TMS) techniques, or deep brain stimulation (DBS) techniques. Accordingly, the particular technique or modality used to treat the patient can depend upon the patient's FA value.

In still further embodiments, the FA value may change over the course of time and/or during the course of treatment. Accordingly, the foregoing techniques may be applied at additional points during the patient's treatment regimen to update the signal delivery location and/or the treatment modality used to affect neurons at the target location. Any of the foregoing techniques may also be used to select or update signal delivery parameters other than the target neural population. Such parameters can include the signal frequency, amplitude (voltage and/or current), polarity (anodal or cathodal) and/or delivery mode (e.g., unipolar or bipolar).

Other techniques may be used in addition to the foregoing techniques to not only identify the target neural population, but identify one or more electrode locations that are expected to deliver signals to the target location in a particular (e.g., efficient) manner. For example, a practitioner can use numerical simulation techniques in combination with structural MRI data to estimate the conductivity of the region around the target neural population. Such techniques typically use the different electrical characteristics of different substances and structures in the brain (e.g., cerebral spinal fluid, neurons, connective tissue, vascular structures and others) to estimate the conductivity of different electrical paths. The practitioner can then select the position of a cortical electrode to be one that results in the shortest and/or lowest conductivity path to the target neural population. It is expected that such an arrangement can reduce the power required to deliver signals to the target neural population, and can accordingly provide stimulation for a greater period of time before it becomes necessary to replace or recharge the power supply that powers the electrodes. This approach can also reduce or eliminate the possibility of misdirected current creating unintended effects at populations other than the target neural population. Similar techniques may also be used to aid the practitioner in aligning the electric field lines generated by one or more electrodes with anatomical features. For example, these techniques can be used to align field lines with the axons of neurons at the target neural population.

Figure 3:
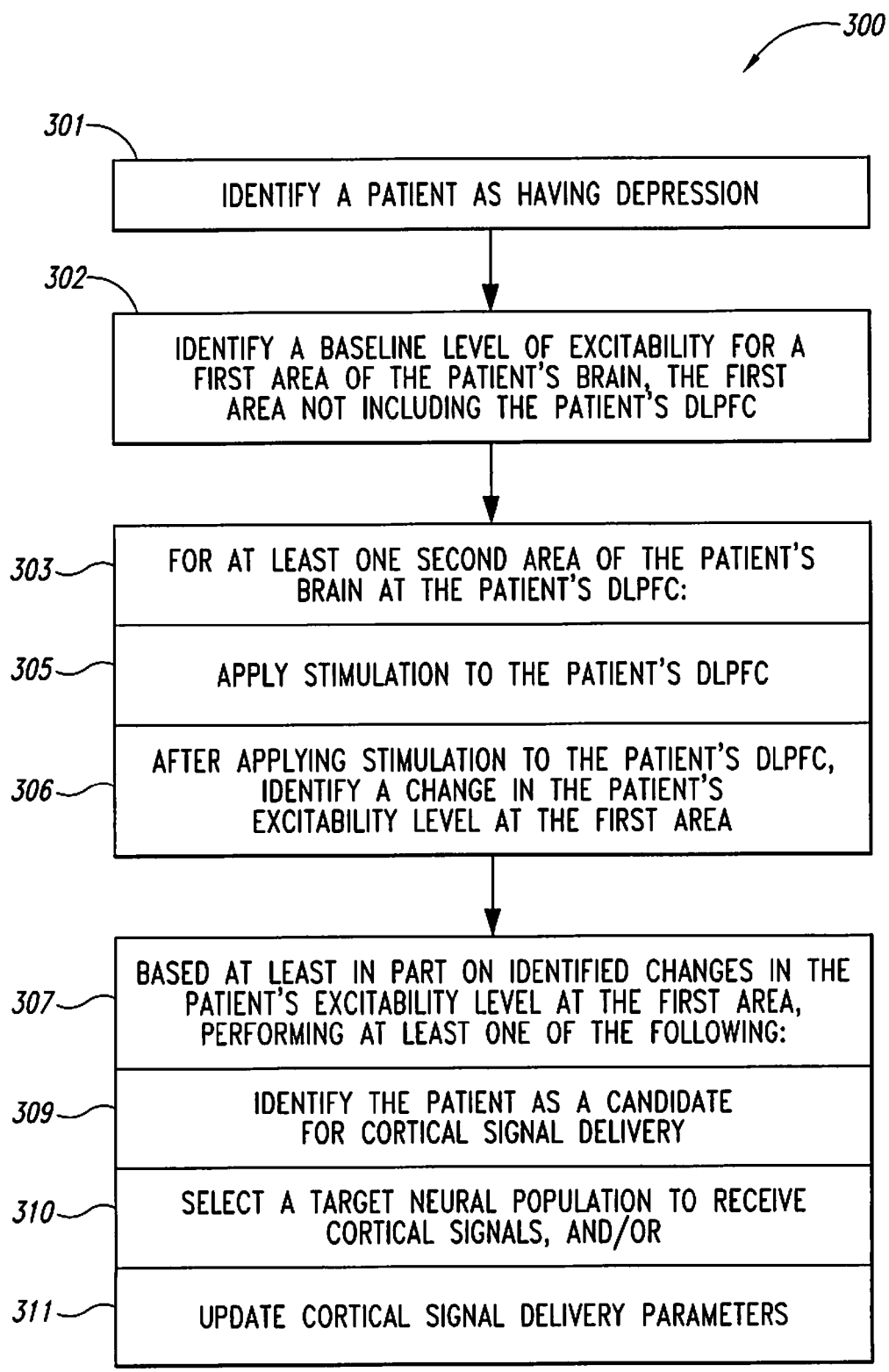
FIG. 3 is a flow diagram illustrating a method for treating a patient's depression in accordance with an embodiment of the disclosure.

FIG. 3 is a flow diagram illustrating a process 300 in accordance with another embodiment of the disclosure. The process 300 can make use of naturally occurring connections between the patient's DLPFC and other areas of the patient's brain to provide information that is then used to screen the patient, identify a target neural population, and/or update signal delivery parameters. In a representative example, once a patient is identified as having depression or another neuropsychological/neuropsychiatric disorder (process portion 301), the practitioner can identify a baseline level of excitability for a first area of the patient's brain that does not include the patient's DLPFC. For example, the first area of the patient's brain can include the patient's motor cortex or sensory cortex. Process portion 303 includes performing several functions for at least one second area of the patient's brain, located at the patient's DLPFC. These functions can include applying stimulation to the patient's DLPFC (process portion 305) and, after applying stimulation to the patient's DLPFC, identifying a change in the patient's excitability level at the first area of the brain (process portion 306). Based at least in part on the identified change in the patient's excitability level at the first area, process portion 307 can include performing any of the following functions: identifying the patient as a candidate for cortical signal delivery (process portion 309), selecting a target neural population to receive cortical signals (process portion 310), and/or updating cortical signal delivery parameters (process portion 311). A representative example implementing an embodiment of the process 300 shown in FIG. 3 is described below with reference to FIG. 4.

Figure 4:
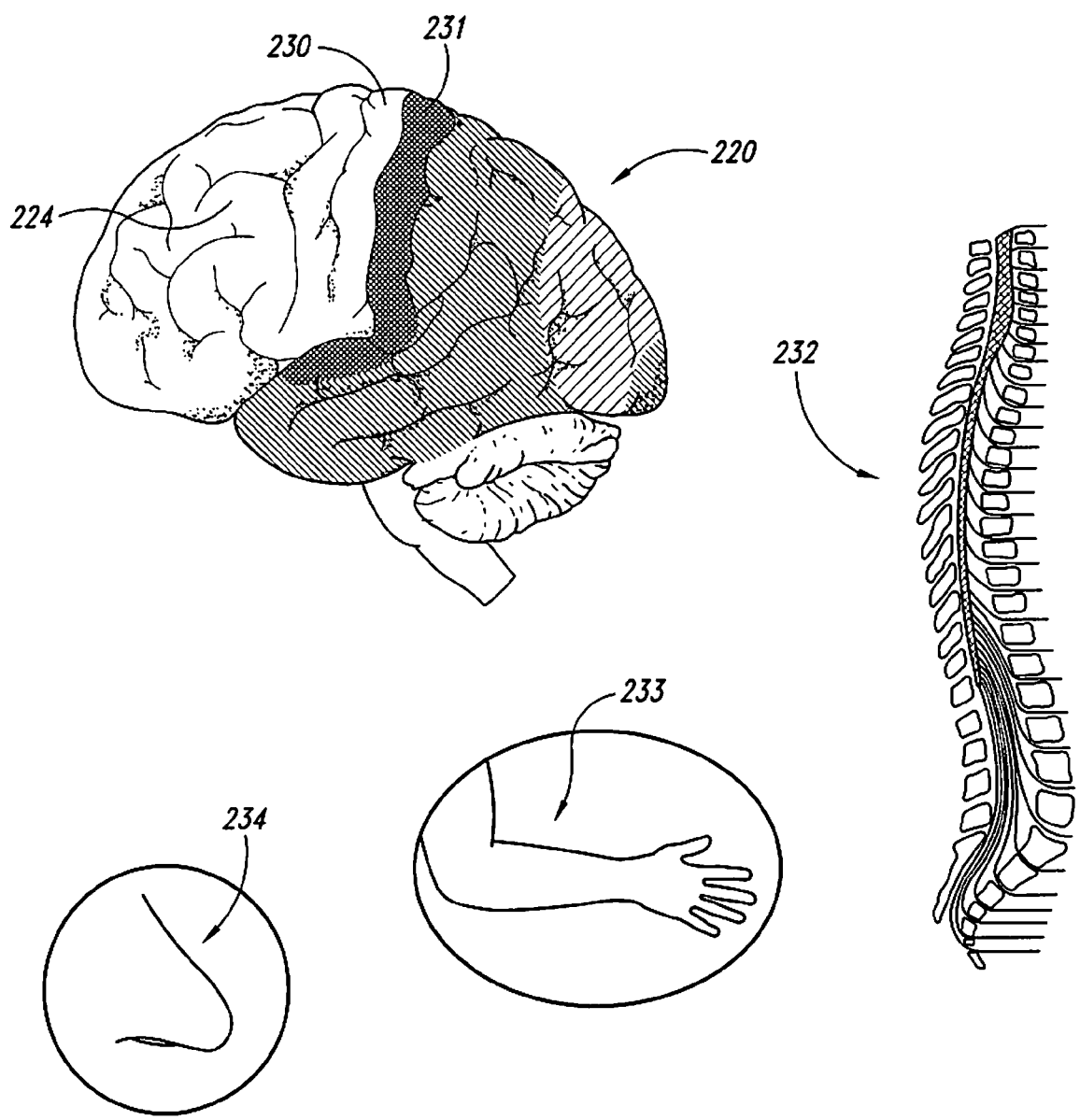
FIG. 4 is a partially schematic illustration of brain and peripheral structures that may be associated with the method shown in FIG. 3.

FIG. 4 is a partially schematic illustration of a portion of the patient's brain 220, identifying the DLPFC 224 and cortical, non-DLPFC brain areas with which the DLPFC 224 communicates. These areas can include the motor cortex 230 and the sensory cortex 231, among others. The motor cortex 230 communicates with one or more of the patient's muscles 233 (e.g., at the patient's arm or hand) via the spinal cord 232. The sensory cortex 231 communicates with one or more of the patient's sensory receptors 234 (e.g., the patient's olfactory nerve). In some cases, e.g. for tactile sensory receptors at the patients trunk or extremities, this communication also occurs via the spinal cord 232. In a representative procedure, the practitioner identifies a baseline level of excitability of the patient's motor cortex, for example, by assessing the patient's response to motor stimuli. The practitioner can then apply excitatory or inhibitory stimuli to the DLPFC 224. For example, the practitioner can apply rTMS signals to the patient for a period of about 20 minutes. After stimulating the DLPFC 224, the practitioner can again assess the patient's level of motor excitability, for example, by applying single-pulse and/or paired-pulse signals (e.g., TMS signals) to the patient's brain and assessing the response level. Single pulse TMS signals may be used to assess a direct effect of the DLPFC on the patient's level of motor excitability, and paired-pulse TMS signals may be used to isolate the effect of inhibitory and/or excitatory interneurons on the patient's level of motor excitability. In any of these embodiments, the foregoing procedure can be repeated for multiple sites at the DLPFC 224, and one or more of these sites can be selected as a target neural population, based upon the effect that stimulation at the site has on the patient's level of motor excitability.

In particular embodiments, it is expected that locations of the DLPFC 224 that have a greater effect on motor excitability than others may be suitable candidates for cortical stimulation. Similar techniques can be used to optimize and/or update the signal delivery parameters used to provide therapy to the patient, after a cortical stimulation device has been implanted in the patient. For example, the effect of the stimulation on the patient's motor excitability at a variety of parameter settings (e.g., stimulation amplitude, polarity, and/or frequency) can be determined and, based upon this determination, particular parameters can be selected or eliminated. The same or a similar technique can be used during the course of the patient's therapy to update signal delivery parameters, for example, as the patient's body adapts to the applied therapy, and/or as the functional level of the target neural population changes as a result of therapy.

Many aspects of the foregoing process can be automated in certain instances. For example, once the patient has received a cortical implant, the patient can also receive one or more implanted sensors located at the motor cortex or sensory cortex, or at the patient's spine (e.g., at a cervical location), or at a peripheral location (e.g., at the patient's muscle or sensory receptor). The sensor(s) can identify changes in the level of excitability at any of these locations and can be coupled to a controller which is in turn coupled to electrodes implanted at the DLPFC. Accordingly, the controller can automatically adjust the signal delivery parameters applied to the electrodes at the DLPFC as the patient's responses to therapeutic signals (or test signals) provided by the electrodes change. This closed-loop arrangement can operate in a semi-automated or fully automated manner to reduce or eliminate the need for the patient or the practitioner to continuously monitor patient performance and/or response to the therapy.

In many instances, it is desirable to compare the state of a patient when the patient is acutely depressed, to a baseline state of the patient. This technique can be used to identify areas of the brain that are active or inactive when a patient is depressed. For example, the practitioner can obtain an image of the patient's brain when the patient is acutely depressed, and compare that image with one obtained when the patient is in a stable or baseline condition. This technique can be used to identify the first region of the brain described above with reference to FIG. 1, or, in particular embodiments (assuming a high degree of resolution), this technique can be used to identify the second region. In any of these cases, the practitioner will obtain an image of the patient's brain or the relevant portion of the patient's brain when the patient is in the baseline or first state, then acutely affect the patient's emotional or cognitive functioning, obtain a second image while the patient is in the second state, and compare the images.

A variety of techniques are expected to be suitable for creating such an effect. For example, rapid tryptophan depletion, which is presently used to identify depression patients suitable for SSRI treatments, can be used to trigger an acute depression condition. Sleep deprivation is another technique that can acutely modulate depression (e.g., it can cause acute remission of depression symptoms), as is hypnosis. In other cases, a patient can be shown sad pictures to induce sadness, depression, or another emotion. In still further cases, multiple sessions of rTMS can acutely modulate the patient's depression response. For example, rTMS can cause a reduction in depression symptoms, or a remission of depression. A variety of imaging/visualization techniques can be used to identify brain areas associated with the acute response. These areas may be hypoactive or hyperactive. Such techniques can include PET scans based on FDG or water analysis, perfusion MRI, connectivity fMRI, and/or task-related fMRI (e.g., in which a patient performs a cognitive or memory task).

In particular cases, the DLPFC or portions of the DLPFC are expected to be hypoperfused and/or hypometabolic when the patient is depressed, and thus a suitable target neural population can be identified using measures of perfusion/blood flow and/or glucose consumption. In other cases, patients with depression or major depressive disorder (MDD) may have reduced glutamate, and/or reduced glutamate/glutamine peaks, and/or reduced choline levels at the frontal cortex, the DLPFC, and/or other cortical regions or subregions. Magnetic resonance spectroscopy (MRS) is expected to be suitable for identifying such areas as target neural populations and/or identifying indications of recovery after therapeutic treatments in accordance with the present disclosure.

In still another embodiment, EEG measurements may be used to identify areas with increased and/or otherwise perturbed activity. For example, EEG measurements may be used to detect increased gamma and/or theta wave activity, which is expected to correlate with depression. In particular cases, EEG measurements can detect changes in brain activity induced by rTMS stimulation.

Representative Stimulation System Embodiments

Figure 5:
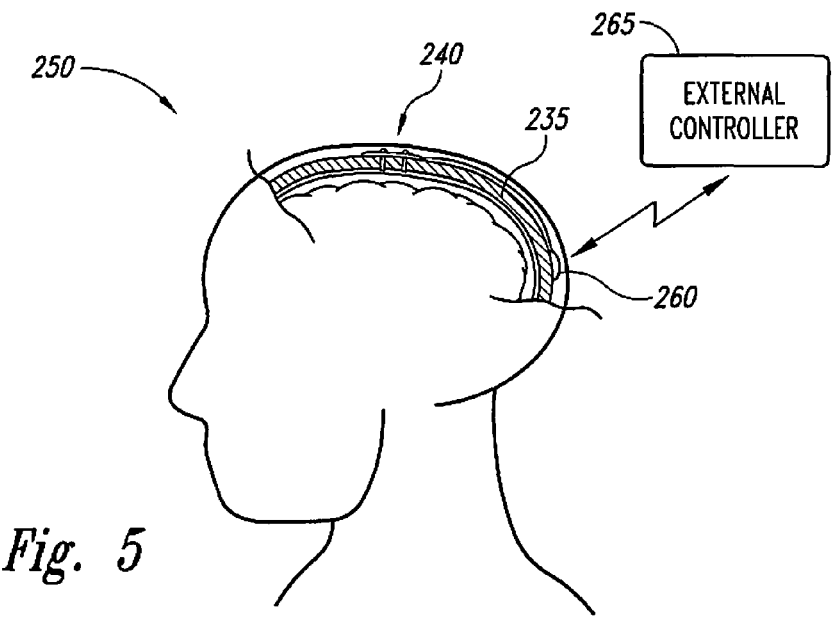
FIG. 5 illustrates an electrode device operatively coupled to an external controller in accordance with an embodiment of the disclosure.

Many aspects of various techniques or procedures described above can be performed by suitable systems configured to deliver cortical stimulation and, in certain cases, stimulation in accordance with other modalities. FIG. 5 schematically illustrates a representative cortical signal delivery system 250. The system 250 can include a pulse system 260 that is positioned external to the patient's skull. For example, as shown in FIG. 5, the pulse system 260 can be placed on the external surface of the patient's skull 235, beneath the scalp. In another arrangement, the pulse system 260 can be implanted at a subclavicular location. The pulse system 260 can be controlled internally via pre-programmed instructions that allow the pulse system 260 to operate autonomously after implantation. In other embodiments, the pulse system 260 can be implanted at other locations, and at least some features of the pulse system 260 can be controlled externally. For example, FIG. 5 illustrates an external controller 265 that controls the pulse system 260.

Figure 6:
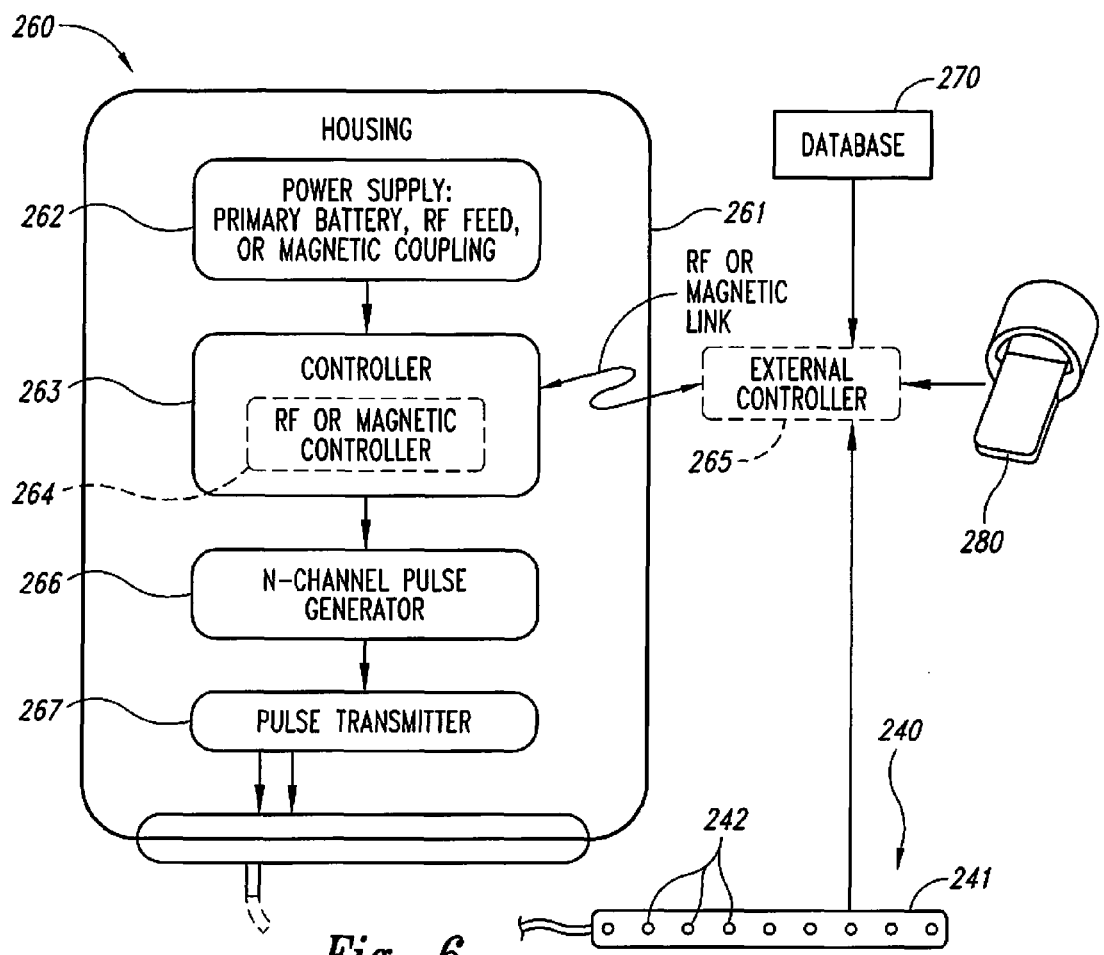
FIG. 6 is a schematic illustration of a pulse system configured in accordance with several embodiments of the disclosure.

FIG. 6 schematically illustrates details of an embodiment of the pulse system 260 described above. The pulse system 260 generally includes a housing 261 carrying a power supply 262, an integrated controller 263, a pulse generator 266, and a pulse transmitter 267. In certain embodiments, a portion of the housing 261 may include a signal return electrode. The power supply 262 can include a primary battery, such as a rechargeable battery, or other suitable device for storing electrical energy (e.g., a capacitor or supercapacitor). In other embodiments, the power supply 262 can include an RF transducer or a magnetic transducer that receives broadcast energy emitted from an external power source and that converts the broadcast energy into power for the electrical components of the pulse system 260.

In one embodiment, the integrated controller 263 can include a processor, a memory, and/or a programmable computer medium. The integrated controller 263, for example, can be a microcomputer, and the programmable computer medium can include software loaded into the memory of the computer, and/or hardware that performs the requisite control functions. In another embodiment identified by dashed lines in FIG. 6, the integrated controller 263 can include an integrated RF or magnetic controller 264 that communicates with the external controller 265 via an RF or magnetic link. In such an embodiment, many of the functions performed by the integrated controller 263 may be resident on the external controller 265 and the integrated portion 264 of the integrated controller 263 may include a wireless communication system.

The integrated controller 263 is operatively coupled to, and provides control signals to, the pulse generator 266, which may include a plurality of channels that send appropriate electrical pulses to the pulse transmitter 267. The pulse transmitter 267 is coupled to a signal delivery device 240, e.g., an electrode device 241 that carries electrodes 242. In one embodiment, each of these electrodes 242 is configured to be physically connected to a separate lead, allowing each electrode 242 to communicate with the pulse generator 266 via a dedicated channel. Accordingly, the pulse generator 266 may have multiple channels, with at least one channel associated with each of the electrodes 242 described above. Suitable components for the power supply 262, the integrated controller 263, the external controller 265, the pulse generator 266, and the pulse transmitter 267 are known to persons skilled in the art of implantable medical devices.

The pulse system 260 can be programmed and operated to adjust a wide variety of stimulation parameters, for example, which electrodes 242 are active and inactive, whether electrical stimulation is provided in a unipolar or bipolar manner, signal polarity, and/or how stimulation signals are varied. In particular embodiments, the pulse system 260 can be used to control the polarity, frequency, duty cycle, amplitude, and/or spatial and/or topographical qualities of the stimulation. Representative signal parameter ranges include a frequency range of from about 0.5 Hz to about 125 Hz, a current range of from about 0.5 mA to about 15 mA, a voltage range of from about 0.25 volts to about 20 volts (e.g., approximately 10 volts), and a first pulse width range of from about 10 μsec to about 500 μsec The stimulation can be varied to match, approximate, or simulate naturally occurring burst patterns (e.g., theta-burst and/or other types of burst stimulation), and/or the stimulation can be varied in a predetermined, pseudorandom, and/or other aperiodic manner at one or more times and/or locations.

In particular embodiments, the pulse system 260 can receive information from selected sources, with the information being provided to influence the time and/or manner by which the signal delivery parameters are varied. For example, the pulse system 260 can communicate with a database 270 that includes information corresponding to reference or target parameter values. Sensors can be coupled to the patient to provide measured or actual values corresponding to one or more parameters. The measured values of the parameter can be compared with the target value of the same parameter. Accordingly, this arrangement can be used in a closed-loop fashion to control when stimulation is provided and when stimulation may cease. In one embodiment, some electrodes 242 may deliver electromagnetic signals to the patient while others are used to sense the activity level of a neural population. In other embodiments, the same electrodes 242 can alternate between sensing activity levels and delivering electrical signals. In either embodiment, information received from the signal delivery device 240 can be used to determine the effectiveness of a given set of signal parameters and, based upon this information, can be used to update the signal delivery parameters and/or halt the delivery of the signals.

In other embodiments, other techniques can be used to provide patient-specific feedback. For example, a detection system or device 280 such as a magnetic resonance chamber can provide information corresponding to the locations at which a particular type of brain activity is occurring and/or the level of functioning at these locations, and can be used to identify additional locations and/or additional parameters in accordance with which electrical signals can be provided to the patient to further increase functionality. Accordingly, the system can include a direction component configured to direct a change in an electromagnetic signal applied to the patient's brain based at least in part on an indication received from one or more sources. These sources can include a detection component (e.g., the signal delivery device and/or the magnetic resonance chamber 280).

Figure 7:
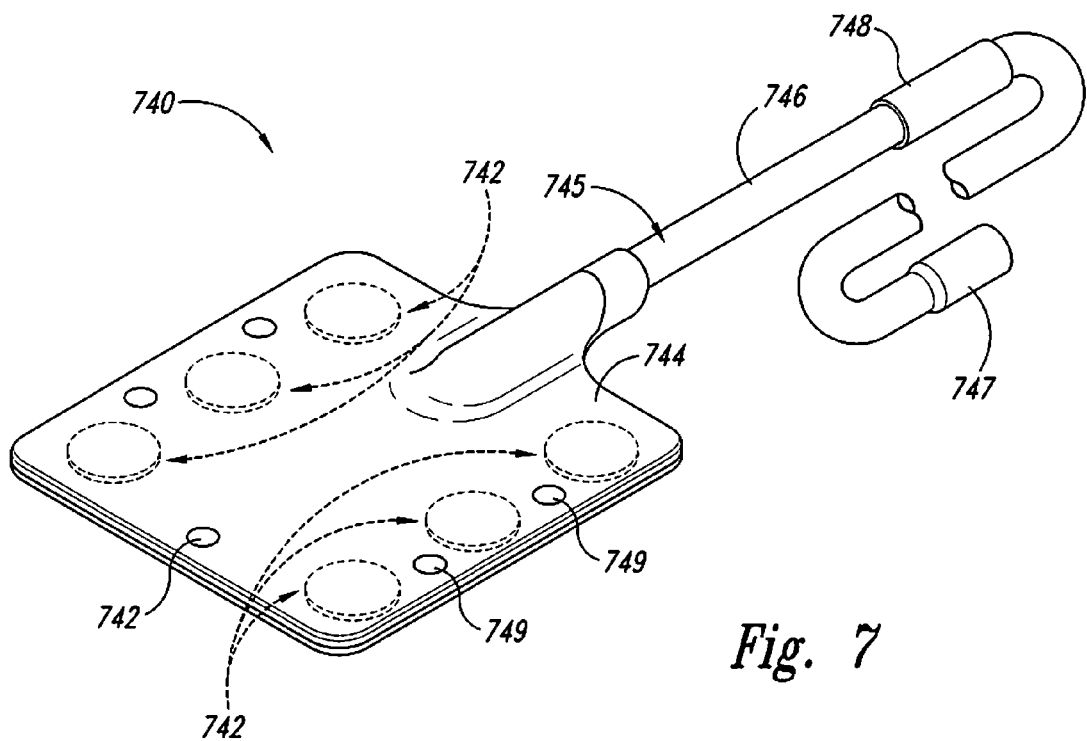
FIG. 7 is an isometric illustration of an electrode device that carries multiple electrodes in accordance with an embodiment of the disclosure.

FIG. 7 is a top, partially hidden isometric view of an embodiment of a signal delivery device 740, configured to carry multiple cortical electrodes 742. The electrodes 742 can be carried by a flexible support member 744 to place each electrode 742 in contact with a stimulation site of the patient when the support member 744 is implanted. Electrical signals can be transmitted to the electrodes 742 via leads carried in a communication link 745. The communication link 745 can include a cable 746 that is connected to the pulse system 260 (FIG. 6) via a connector 747, and is protected with a protective sleeve 748. Coupling apertures or holes 749 can facilitate temporary attachment of the signal delivery device 740 to the dura mater at, or at least proximate to, a stimulation site. The electrodes 742 can be biased cathodally and/or anodally. In an embodiment shown in FIG. 7, the signal delivery device 740 can include six electrodes 742 arranged in a 2×3 electrode array (i.e., two rows of three electrodes each), and in other embodiments, the signal delivery device 740 can include more or fewer electrodes 742 arranged in symmetrical or asymmetrical arrays. The particular arrangement of the electrodes 742 can be selected based on the region of the patient's brain that is to be stimulated, and/or the patient's condition.

Figure 8A:
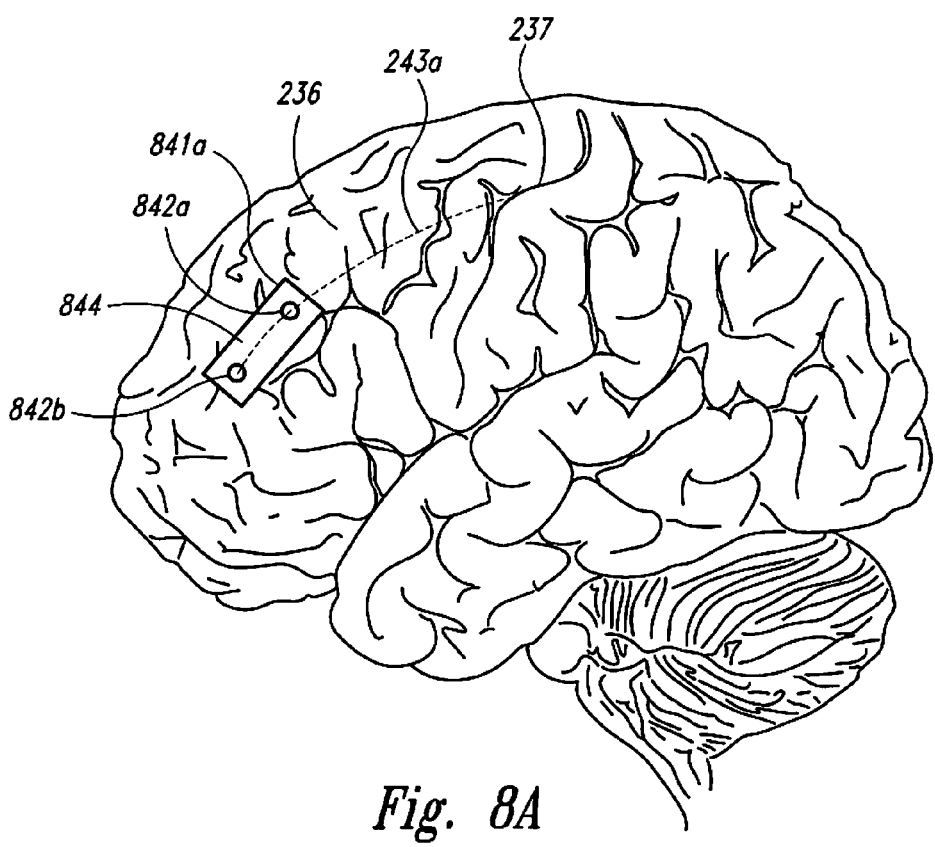
FIGS. 8A-8C are partially schematic illustrations of electrode devices implanted at locations selected in accordance with embodiments of the disclosure.

FIG. 8A is a schematic illustration of a first electrode device 841a implanted above or upon a patient's middle frontal gyrus 236 in accordance with an embodiment of the disclosure. The first electrode device 841a includes a first electrode 842a and a second electrode 842b that are carried by a substrate or support member 844. The first and second electrodes 841a, 841b are coupled to a pulse generator (not shown) in a manner understood by one of ordinary skill in the art. In this embodiment, each electrode 842a, 842b is generally circular. Depending upon embodiment details, such electrodes 842a, 842b can be approximately 0.5-4.5 mm (e.g., 3.75 mm) in diameter, and can have a center-to-center spacing of approximately 10-40 mm (e.g., 15 mm, 18 mm, or another separation distance). The centers of the first electrode 842a and the second electrode 842b can be positioned to approximately intersect or reside along or proximate to a line or an arc 243a that generally bisects at least a portion of the middle frontal gyrus 236 into superior and inferior portions. The particular position along line 243a can be determined by any of the foregoing techniques directed to identifying target neural populations and associated stimulation sites (e.g., electrode placement sites). Such techniques can also be used to place the electrodes at other cortical locations, including, but not limited to, those described below with reference to FIGS. 8B-8C.

Figure 8B:
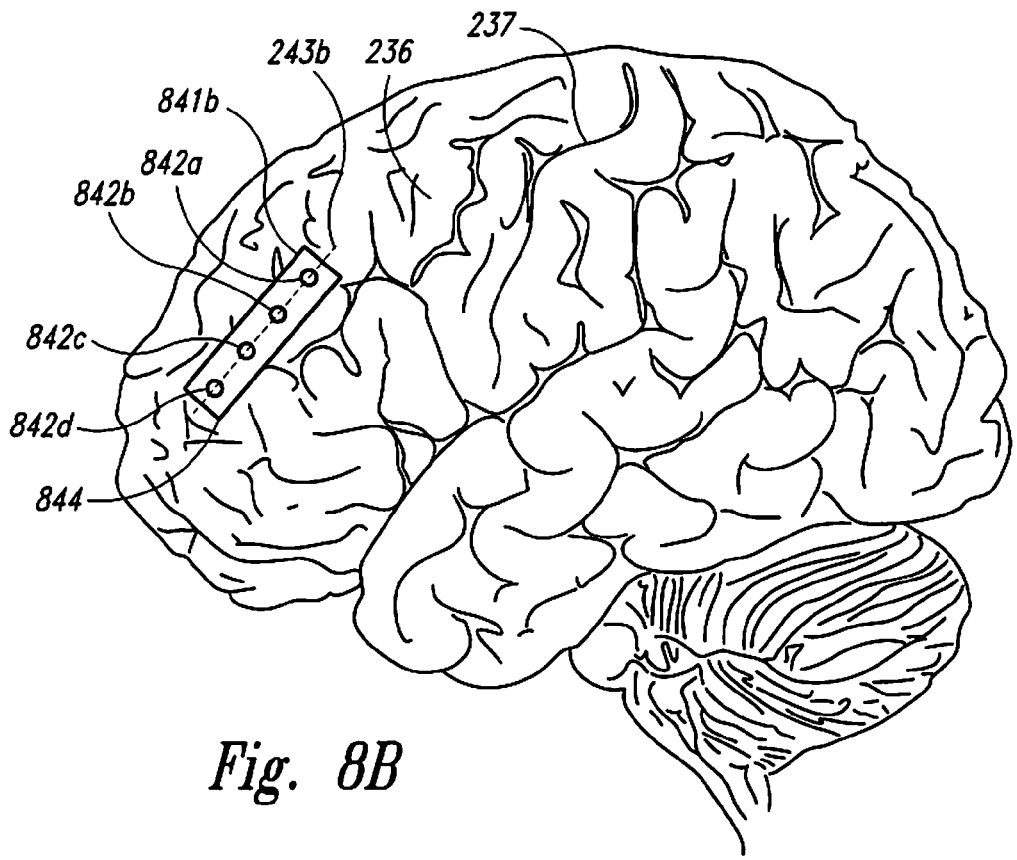

FIG. 8B is a schematic illustration of a second electrode device 841*b* implanted above or upon a patient's middle frontal gyrus 236 in accordance with another embodiment of the previously described surgical implantation protocol. The second electrode device 841*b* includes a support member 844 that carries a first, a second, and a third electrode 842*a*, 842*b*, 842*c* and possibly an nth electrode 842*d*, where n is greater than or equal to 4. In several embodiments, the second electrode device 841*b* can be positioned such that as many electrodes 842*a*-842*d* as possible reside above, along, or proximate to a line or an arc 243*b* that generally bisects at least a portion of the middle frontal gyrus 236 as the line or arc 243*b* extends between the middle frontal gyrus 236 and the central sulcus 237 in an anterior-posterior direction.

Figure 8C:
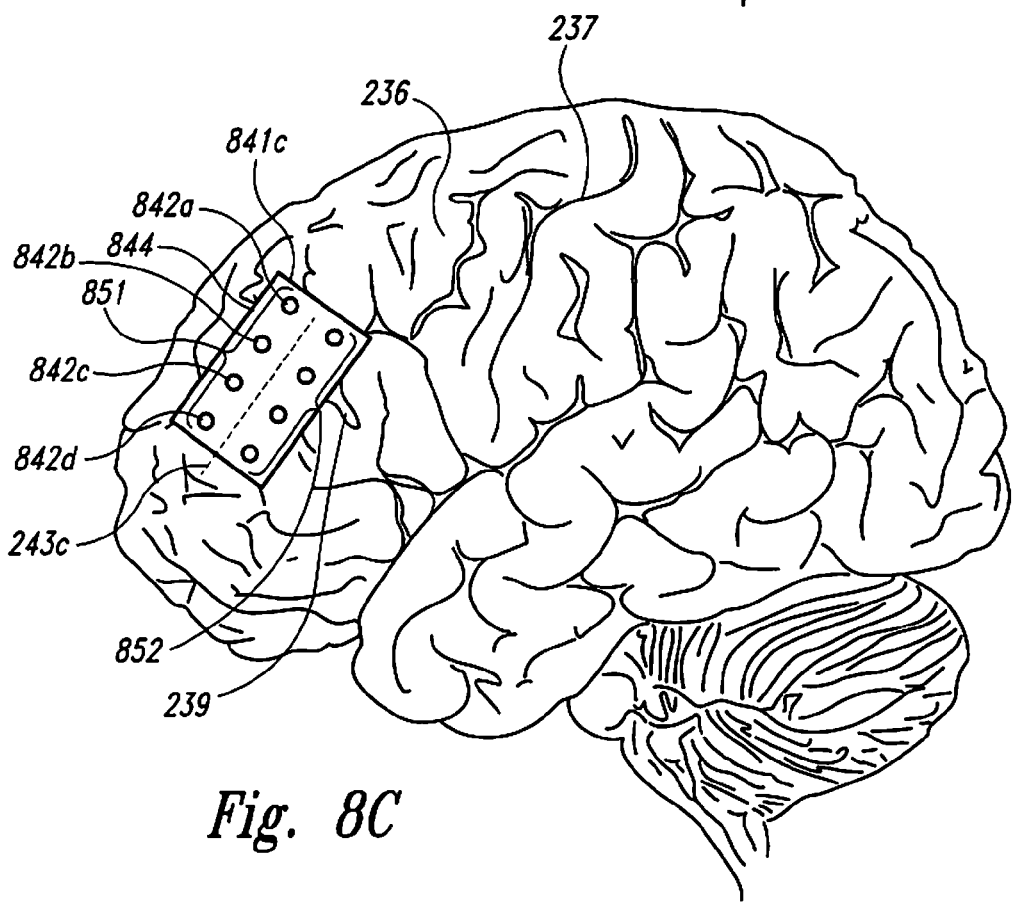

FIG. 8C is a schematic illustration of a third electrode device 841*c* implanted above or upon a patient's middle frontal gyrus 236 in accordance with yet another embodiment of the aforementioned surgical implantation protocol. The third electrode assembly 841*c* includes a support member 844 that carries a first and a second row of electrodes 851, 852, where each electrode row 851, 852 includes at least a first electrode 842*a* and possibly up to an $n^{th}$ electrode 842*d*. The third electrode device 841*c* can be positioned such that each electrode row 851, 852 is approximately equidistant from a line or arc 243*c* that extends anteriorly from the central sulcus 237 and which approximately bisects a portion of the middle frontal gyrus 236; or such that a superior and an inferior electrode row 851, 852 are approximately equidistant from the superior frontal sulcus 238 and the inferior frontal sulcus 239, respectively.

In some embodiments, the electrode device 841*c* can include electrodes 842*a*-842*d* that are arranged, organized, or positioned in a curvilinear or arcuate manner rather than in a linear manner. An arc along which electrodes 842*a*-842*d* are positioned can be predefined such that the electrodes carried by an as-manufactured electrode device will conform or approximate conform to the curvature of a particular portion or section of a neuroanatomical structure, such as the crown of the middle frontal gyrus spanning Brodmann areas 9, 46, and/or 9/46.

A stimulation procedure directed toward the application of extrinsic stimulation signals to treat neuropsychiatric dysfunction can include one or more time periods in which each electrode of a given electrode assembly is electrically active. Additionally or alternatively, a stimulation procedure can include one or more time periods in which particular electrode subsets carried by a given electrode assembly are electrically active. The activation of each electrode and/or one or more electrode subsets can depend upon the type of neurologic dysfunction under consideration and/or the patient's clinical response, imaging response, and/or electrophysiologically measured (e.g., ECoG) response to the applied stimulation signals.

In a representative example, the electrode device 841*b* shown in FIG. 8B can have an initially active electrode subset that includes the first, second, and third electrodes 841*a*-841*c*. Depending upon the nature and/or extent of a patient's response to the extrinsic stimulation signals (for instance, the presence or absence of a noticeable or favorable acute response, and/or the presence or absence of a beneficial or adverse response that arises over the course of a number of weeks (e.g., 2-12 weeks)), additional, one or more anterior electrodes 841*d* can be activated at one or more times. Moreover, one or more most-posterior electrodes 841*a*, 841*b* can be deactivated at one or more times, and/or stimulation signals applied to such more-posterior electrodes 841*a*, 841*b* at a reduced intensity or level in the event that clinical, imaging, and/or electrophysiologic data indicates that such electrodes 841*a*, 841*b* provide relatively less or little contribution to therapeutic efficacy.

In a representative embodiment, the third electrode device 841*c* shown in FIG. 8C can include any given electrode subset that is active at one or more times, with active electrodes located in one or both electrode rows 851, 852. In certain situations, an initial set or subset of electrodes carried by an electrode device can be used to initially apply stimulation signals. Depending upon embodiment details, the initial set of electrodes can include some or all of the electrodes carried by the electrode device. After a first time period during which the patient experiences a favorable therapeutic response, particular electrodes (e.g., one or more most-posterior electrodes) within the initial set of electrodes can be activated at a reduced signal intensity, level, or duration, or deactivated during a second time period, and the patient monitored to determine whether a sufficiently high or adequate level of therapeutic benefit is present. Such a stimulation procedure can successively, over time, determine a minimum number of active electrodes that are useful for achieving or maintaining therapeutic efficacy. In the event that therapeutic efficacy changes or degrades over time following a generally stable period of therapeutic benefit, the foregoing stimulation procedure can be repeated, or additional electrodes can be successively (re) activated, until a sufficient or desired level of therapeutic benefit occurs. For example, the patient's neuropsychological stability may be adversely affected after several months, such as 6 or 12 months, possibly due to an event in the patient's life.

In several embodiments, a threshold signal intensity or level corresponding to a given electrode subset can be determined by applying stimulation signals to this electrode subset, and measuring or estimating a minimum or near-minimum stimulation signal level that gives rise to a predetermined or minimum degree of change in neurocognitive task performance. A treatment signal intensity or level that is applied to the patient during a therapy period can be based upon a threshold signal level corresponding to one or more electrode subsets. For instance, a treatment signal level can be a given percentage of (e.g., approximately 20-95%, or approximately 50%, 80%, or 90% of) the activation threshold signal level corresponding to the particular electrode subset that gave rise to the lowest threshold signal level relative to each electrode subset considered. The threshold level can correspond to a level (e.g., current level or voltage level) that causes action potentials in a large enough portion of the target neural population to produce the patient function associated with the target neural population. During a therapy period, a treatment signal can be applied to the particular electrode subset that gave rise to this lowest threshold level, and/or one or more other electrode subsets. In addition or as an alternative to the foregoing, a treatment signal intensity can be a mathematical function such as an average or a weighted average of a plurality of threshold signal intensities, where in some embodiments a weighting function can prioritize a threshold signal intensity associated with neurons in particular neural locations (e.g., more anterior neurons) more heavily than a threshold signal intensity associated with neurons within other (e.g., more posterior) neural locations. In yet other embodiments, a treatment signal can be or include a set of pulses that are delivered approximately at or even slightly above a threshold or expected threshold level.

Many of the foregoing embodiments include techniques for identifying a target neural population, a target stimulation site, stimulation parameters, stimulation modalities, and/or suitable patients using functional techniques, alone or in combination with techniques based on the structure of the patient's brain. An expected advantage of these techniques is that they can more accurately identify characteristics associated with a stimulation therapy than can techniques that rely on brain structure alone. In some cases, these techniques can eventually be correlated with brain structures that are common from one patient to the next and, in such cases, a practitioner can revert back to site identification and/or other parameter selection on the basis of one or more structures that are defined with a new level of precision. In other cases, the foregoing techniques can continue to be used on a patient-by-patient basis to more accurately identify the stimulation characteristics.

From the foregoing, it will be appreciated that specific embodiments of the disclosure have been described herein for purposes of illustration, but that various modifications may be made in other embodiments. For example, the practitioner may use structurally based and/or functionally based techniques that differ from those specifically described above. The practitioner may use more than two levels of information to identify target neural populations in at least some cases. In some cases, the practitioner may produce an actual image upon which to base a parameter selection, and in other cases, at least some aspects of the parameter selection may be automated and/or may rely on the underlying data used to produce the image without actually producing the image itself. For example, fractional anisotropy levels may be determined without the need for an actual image, and regions of high tract density may be correlated with a location in space (referenced to a fiducial or anatomic feature) again, without the need for an actual image. The signals applied in any of the foregoing methods can have a direct effect on the target neural population that lasts for as long as the signal is active, or a long-term effect that can enhance, enable, augment and/or otherwise facilitate the patient's natural neuroplastic responses. Such long term effects can last for days, weeks, months or years after the stimulation has ceased.

Several examples were described above in the context of depression, but the same or generally similar methodologies can be used to address other neuropsychiatric/neuropsychological conditions, including post-traumatic stress disorder (PTSD), eating disorders and others identified previously. In still further embodiments, the foregoing methods can be applied to patients without disorders, e.g. to improve the cognitive functioning of a normal or above-normal patient. Many of the foregoing techniques may be applied on a case-by-case basis that is specific to individual patients. However, as discussed above, after a sufficient database (e.g., group atlas) has been established as a result of collecting individual data, practitioners may in some cases be able to circumvent certain steps over the course of time. For example, practitioners may find that for certain conditions (e.g., certain types of depression), the same area of the DLPFC, (as identified by anatomical landmarks), is always or nearly always a suitable target neural population.

Several examples were provided above with reference to specific brain areas (e.g., Brodmann areas 10 and 25) and/or specific loops (e.g., thalamocortical loops). In other embodiments, similar techniques can be applied to other areas. For example, when treating depression, the anterior cingulate cortex (ACC) may be identified as a non-superficial component of the thalamocortical loop that also includes the DLPFC. Accordingly, target cortical neural populations may be selected on the basis of tract density descending to the ACC.

Certain aspects of the invention described in the context of particular embodiments may be combined or eliminated in other embodiments. For example, aspects of the technique described in the context of FIG. 1 may be combined with aspects of the technique described in FIG. 3. Further, while advantages associated with certain embodiments have been described in the context of those embodiments, other embodiments may also exhibit such advantages and not all embodiments need necessarily exhibit such advantages to fall within the scope of the present disclosure.

We claim:

1. A method for treating a patient, comprising:
obtaining first imaging information corresponding to a first region of a patient's brain, the first imaging information being based at least in part on functional characteristics of the first region;
obtaining second imaging information corresponding to a second region of the patient's brain, the second region being a subset of the first region, the second imaging information being based at least in part on functional or structural characteristics of the second region;
selecting a target neural population based at least in part on the second imaging information; and
applying an electromagnetic signal to the target neural population to improve a patient function;
wherein obtaining first imaging information includes obtaining first imaging information of the patient's middle frontal gyrus.

2. The method of claim 1 wherein obtaining second imaging information includes obtaining second imaging information having a higher resolution than the first imaging information.

3. The method of claim 1 wherein obtaining second imaging information includes obtaining at least one of fractional anisotropy information and diffusion tensor imaging information.

4. The method of claim 1 wherein obtaining first imaging information includes obtaining first imaging information using fMRI techniques.

5. The method of claim 4 wherein obtaining first imaging information includes obtaining first information on a real-time or approximately real-time basis, and wherein obtaining the second information includes using spectroscopy techniques while the patient is present.

6. The method of claim 1 wherein obtaining second imaging information includes obtaining information including a thickness value of gray matter in the second region.

7. The method of claim 1, further comprising identifying the patient as having depression, and wherein:
obtaining first imaging information includes obtaining functional magnetic resonance imaging information while engaging the patient in a task selected to trigger an emotional response in the patient, the first imaging information having a first resolution; and wherein
obtaining second imaging information includes obtaining diffusion tensor imaging information having a second resolution greater than the first resolution, and wherein the method further comprises obtaining a fractional anisotropy level for the patient, and, based at least in part on the fractional anisotropy level, determining whether the patient is a suitable candidate for receiving an electromagnetic signal; and wherein
applying an electromagnetic signal includes applying an electrical signal from an electrode positioned within the patient's skull cavity and outside a cortical surface of the patient's brain.

8. A method for treating a patient, comprising:
identifying a patient as having depression;
obtaining first imaging information corresponding to a first region of a patient's brain, the first imaging information being obtained by functional magnetic resonance imaging techniques, the first region including the patient's DLPFC;
obtaining second imaging information corresponding to a second region of the patient's brain, the second region being a subset of the first region, the second imaging information being based at least in part on identifying neuronal fibers using diffusion tractography techniques;
selecting a signal delivery site based at least in part on the second imaging information;
implanting at least one electrode proximate to the signal delivery site, within the patient's skull and outside a cortical surface of the patient's brain; and
reducing or eliminating patient depression by preferentially directing electrical signals from the at least one electrode to the signal delivery site;
wherein selecting a signal delivery site includes selecting a signal delivery site based at least in part on a characteristic of neuronal fibers projecting from the signal delivery site to Brodmann area 25.

9. The method of claim 8 wherein obtaining second imaging information includes obtaining a number of neuronal tracts.

10. The method of claim 8 wherein obtaining second imaging information includes obtaining a density of neuronal tracts.

11. The method of claim 8 wherein obtaining first imaging information includes obtaining first imaging information while the patient performs a working memory task.

12. The method of claim 8 wherein obtaining first imaging information includes obtaining first imaging information while the patient is exposed to an emotional trigger stimulus.

13. The method of claim 8, further comprising obtaining a fractional anisotropy level for the patient, and, based at least in part on the fractional anisotropy level, determining whether the patient is a suitable candidate for receiving an electromagnetic signal.

14. The method of claim 13 wherein determining includes determining that the fractional anisotropy level is below an average value for a generalized patient population, and above a threshold value.

* * * * *